US009066410B2

(12) United States Patent
Breuning

(10) Patent No.: US 9,066,410 B2
(45) Date of Patent: Jun. 23, 2015

(54) ORGANIC ELECTRONIC DEVICE

(75) Inventor: Esther Breuning, Ober-Ramstadt (DE)

(73) Assignee: Merck Patent GmbH (DE)

(*) Notice: Subject to any disclaimer, the term of this patent is extended or adjusted under 35 U.S.C. 154(b) by 931 days.

(21) Appl. No.: 13/201,981

(22) PCT Filed: Jan. 20, 2010

(86) PCT No.: PCT/EP2010/000330
§ 371 (c)(1),
(2), (4) Date: Aug. 17, 2011

(87) PCT Pub. No.: WO2010/094378
PCT Pub. Date: Aug. 26, 2010

(65) Prior Publication Data
US 2011/0297925 A1 Dec. 8, 2011

(30) Foreign Application Priority Data
Feb. 17, 2009 (DE) .................. 10 2009 009 277

(51) Int. Cl.
H01L 51/54 (2006.01)
H05B 33/14 (2006.01)
C07D 221/14 (2006.01)
C07D 259/00 (2006.01)
H01L 51/50 (2006.01)
C09K 11/06 (2006.01)
H01L 51/00 (2006.01)
C09B 57/00 (2006.01)
C09B 1/00 (2006.01)
C09B 3/02 (2006.01)
C09B 3/22 (2006.01)

(52) U.S. Cl.
CPC .............. H05B 33/14 (2013.01); C07D 221/14 (2013.01); C07D 259/00 (2013.01); H01L 51/5088 (2013.01); C09K 11/06 (2013.01); C09K 2211/1029 (2013.01); C09K 2211/1074 (2013.01); C09K 2211/1081 (2013.01); C09K 2211/1466 (2013.01); C09K 2211/1475 (2013.01); C09K 2211/1483 (2013.01); C09K 2211/1491 (2013.01); H01L 51/0072 (2013.01); C09B 57/00 (2013.01); C09B 57/008 (2013.01); C09B 1/00 (2013.01); C09B 3/02 (2013.01); C09B 3/22 (2013.01); Y02E 10/549 (2013.01); H01L 51/5072 (2013.01)

(58) Field of Classification Search
CPC ............ H01L 51/0072; H01L 51/5072; H01L 51/5088; C09K 11/06; C09K 2211/1018; C09K 2211/1022; C07D 221/14; C07D 259/00
See application file for complete search history.

(56) References Cited

U.S. PATENT DOCUMENTS

| 3,089,875 | A | 5/1963 | Schroeder |
|---|---|---|---|
| 4,539,507 | A | 9/1985 | VanSlyke et al. |
| 4,780,536 | A | 10/1988 | Czarnik et al. |
| 5,061,569 | A | 10/1991 | VanSlyke et al. |
| 5,151,629 | A | 9/1992 | VanSlyke |
| 5,621,131 | A | 4/1997 | Kreuder et al. |
| 5,837,166 | A | 11/1998 | Kawamura et al. |
| 5,840,217 | A | 11/1998 | Lupo et al. |
| 5,935,721 | A | 8/1999 | Shi et al. |
| 6,344,283 | B1 | 2/2002 | Inoue et al. |
| 6,458,909 | B1 | 10/2002 | Spreitzer et al. |
| 6,653,438 | B1 | 11/2003 | Spreitzer et al. |
| 7,728,137 | B2 | 6/2010 | Stoessel et al. |
| 2004/0076853 | A1* | 4/2004 | Jarikov ..................... 428/690 |
| 2004/0247937 | A1 | 12/2004 | Chen et al. |
| 2005/0069729 | A1 | 3/2005 | Ueda et al. |
| 2005/0181232 | A1 | 8/2005 | Ricks et al. |
| 2005/0211958 | A1 | 9/2005 | Conley et al. |
| 2005/0260442 | A1 | 11/2005 | Yu et al. |
| 2006/0035109 | A1 | 2/2006 | Arakane et al. |
| 2006/0063027 | A1 | 3/2006 | Vestweber et al. |
| 2006/0175958 | A1 | 8/2006 | Gerhard et al. |
| 2006/0202190 | A1 | 9/2006 | Funahashi |
| 2006/0208221 | A1 | 9/2006 | Gerhard et al. |
| 2006/0210830 | A1 | 9/2006 | Funahashi et al. |
| 2006/0284140 | A1 | 12/2006 | Breuning et al. |
| 2007/0060736 | A1 | 3/2007 | Becker et al. |
| 2007/0082284 | A1 | 4/2007 | Stoessel et al. |
| 2007/0170419 | A1 | 7/2007 | Gerhard et al. |
| 2007/0176147 | A1 | 8/2007 | Buesing et al. |
| 2007/0205714 | A1 | 9/2007 | Busing et al. |
| 2007/0249834 | A1 | 10/2007 | Stossel et al. |
| 2007/0281182 | A1 | 12/2007 | Schulte et al. |
| 2008/0027220 | A1 | 1/2008 | Stossel et al. |

(Continued)

FOREIGN PATENT DOCUMENTS

| DE | 102004047257 A1 | 4/2006 |
|---|---|---|
| DE | 102008024182 | 11/2009 |
| DE | 102008027005 | 12/2009 |
| DE | 102008033943 | 1/2010 |
| DE | 102008035413 | 2/2010 |

(Continued)

OTHER PUBLICATIONS

Boudou, J., et al., "Organic nitrogen chemistry during low-grade metamorphism," Geochimica et Cosmochimica Acta (2008), vol. 72, pp. 1199-1221.

(Continued)

Primary Examiner — Michael H Wilson
(74) Attorney, Agent, or Firm — Drinker Biddle & Reath LLP

(57) ABSTRACT

The present invention relates to organic electroluminescent devices which comprise aromatic nitrogen heterocyclic compounds, in particular in a hole-injection layer and/or in a hole-blocking layer and/or in an electron-transport layer and/or or in an emitting layer.

19 Claims, No Drawings

(56) References Cited

U.S. PATENT DOCUMENTS

| | | |
|---|---|---|
| 2008/0039624 A1 | 2/2008 | Gmeiner et al. |
| 2008/0125609 A1 | 5/2008 | Vestweber et al. |
| 2008/0145698 A1 | 6/2008 | Heil et al. |
| 2008/0161567 A1 | 7/2008 | Stoessel et al. |
| 2008/0193398 A1* | 8/2008 | Trullas et al. .................. 424/59 |
| 2008/0220285 A1 | 9/2008 | Vestweber et al. |
| 2008/0272693 A1 | 11/2008 | Heil et al. |
| 2008/0303417 A1 | 12/2008 | Yabunouchi et al. |
| 2008/0303423 A1 | 12/2008 | Heil et al. |
| 2009/0005505 A1 | 1/2009 | Buesing et al. |
| 2009/0058289 A1 | 3/2009 | Stoessel et al. |
| 2009/0066225 A1 | 3/2009 | Kimura et al. |
| 2009/0072712 A1 | 3/2009 | Stoessel et al. |
| 2009/0134384 A1 | 5/2009 | Stoessel et al. |
| 2009/0159874 A1 | 6/2009 | Vestweber et al. |
| 2009/0167166 A1 | 7/2009 | Bach et al. |
| 2009/0184313 A1 | 7/2009 | Buesing et al. |
| 2009/0226759 A1 | 9/2009 | Heun et al. |
| 2009/0261717 A1 | 10/2009 | Buesing et al. |
| 2009/0292080 A1 | 11/2009 | Stossel et al. |
| 2009/0302742 A1 | 12/2009 | Komori et al. |
| 2009/0302752 A1 | 12/2009 | Parham et al. |
| 2010/0102305 A1 | 4/2010 | Heun et al. |
| 2010/0141129 A1 | 6/2010 | Fukuoka et al. |
| 2010/0187505 A1 | 7/2010 | Stoessel et al. |
| 2010/0187977 A1 | 7/2010 | Kai et al. |
| 2010/0193773 A1 | 8/2010 | Yamamoto et al. |
| 2010/0227978 A1 | 9/2010 | Stoessel et al. |
| 2010/0244009 A1 | 9/2010 | Parham et al. |
| 2010/0288974 A1 | 11/2010 | Buesing et al. |
| 2010/0331506 A1 | 12/2010 | Fortte et al. |
| 2011/0034744 A1 | 2/2011 | Ikeda et al. |
| 2011/0068304 A1 | 3/2011 | Parham et al. |
| 2011/0089410 A1 | 4/2011 | Stoessel et al. |
| 2011/0092701 A1 | 4/2011 | Pflumm et al. |
| 2011/0108821 A1 | 5/2011 | Kaiser et al. |
| 2011/0121274 A1 | 5/2011 | Parham et al. |
| 2011/0140043 A1 | 6/2011 | Stoessel et al. |

FOREIGN PATENT DOCUMENTS

| | | |
|---|---|---|
| DE | 102008036982 | 2/2010 |
| DE | 102009005746 A1 | 7/2010 |
| EP | 650955 A1 | 5/1995 |
| EP | 0 676 461 A2 | 10/1995 |
| EP | 0681019 A2 | 11/1995 |
| EP | 0 707 020 A2 | 4/1996 |
| EP | 0 842 208 A1 | 5/1998 |
| EP | 0891121 A1 | 1/1999 |
| EP | 0 894 107 A1 | 2/1999 |
| EP | 1 028 136 A2 | 8/2000 |
| EP | 1 191 612 A2 | 3/2002 |
| EP | 1 191 613 A2 | 3/2002 |
| EP | 1 191 614 A2 | 3/2002 |
| EP | 1205527 A1 | 5/2002 |
| EP | 1617710 A1 | 1/2006 |
| EP | 1617711 A1 | 1/2006 |
| EP | 1661888 A1 | 5/2006 |
| EP | 1731584 A1 | 12/2006 |
| EP | 1854797 A1 | 11/2007 |
| EP | 2276723 A1 | 1/2011 |
| EP | 2294160 A2 | 3/2011 |
| EP | 2303815 A1 | 4/2011 |
| EP | 2307520 A1 | 4/2011 |
| EP | 2311111 A1 | 4/2011 |
| GB | 1333128 A | 10/1973 |
| JP | 06/001973 A | 1/1994 |
| JP | 2000/053957 A | 2/2000 |
| JP | 2000/273056 A | 10/2000 |
| JP | 2001/226331 A | 8/2001 |
| JP | 2004/288381 A | 10/2004 |
| JP | 2005-347160 A | 12/2005 |
| JP | 2006/253445 A | 9/2006 |
| SU | 1747448 A1 | 7/1992 |
| WO | WO-92/18552 A1 | 10/1992 |
| WO | WO-95/09147 A1 | 4/1995 |
| WO | WO-97/05184 A1 | 2/1997 |
| WO | WO-97/39045 A1 | 10/1997 |
| WO | WO-98/27136 A1 | 6/1998 |
| WO | WO-98/30071 A1 | 7/1998 |
| WO | WO-00/22026 A1 | 4/2000 |
| WO | WO-00/70655 A2 | 11/2000 |
| WO | WO-01/21698 A1 | 3/2001 |
| WO | WO-01/41512 A1 | 6/2001 |
| WO | WO-01/49806 A1 | 7/2001 |
| WO | WO-02/02714 A2 | 1/2002 |
| WO | WO-02/15645 A1 | 2/2002 |
| WO | WO-03/060956 A2 | 7/2003 |
| WO | WO-2004/013080 A1 | 2/2004 |
| WO | WO-2004/018587 A1 | 3/2004 |
| WO | WO-2004/028217 A1 | 4/2004 |
| WO | WO-2004/041901 A1 | 5/2004 |
| WO | WO-2004/047499 A1 | 6/2004 |
| WO | WO-2004/058911 A2 | 7/2004 |
| WO | WO-2004/070772 A2 | 8/2004 |
| WO | WO-2004/080975 A1 | 9/2004 |
| WO | WO-2004/081017 A1 | 9/2004 |
| WO | WO-2004/092111 A1 | 10/2004 |
| WO | WO-2004/093207 A2 | 10/2004 |
| WO | WO-2004/113412 A2 | 12/2004 |
| WO | WO-2004/113468 A1 | 12/2004 |
| WO | WO-2005/011013 A1 | 2/2005 |
| WO | WO-2005/014689 A2 | 2/2005 |
| WO | WO-2005/033244 A1 | 4/2005 |
| WO | WO-2005/039246 A1 | 4/2005 |
| WO | WO-2005/040302 A1 | 5/2005 |
| WO | WO-2005/042550 A1 | 5/2005 |
| WO | WO-2005/084081 A1 | 9/2005 |
| WO | WO-2005/084082 A1 | 9/2005 |
| WO | WO-2005/104264 A1 | 11/2005 |
| WO | WO-2005/111172 A2 | 11/2005 |
| WO | WO-2005/113563 A1 | 12/2005 |
| WO | WO-2006/000388 A1 | 1/2006 |
| WO | WO-2006/000389 A1 | 1/2006 |
| WO | WO-2006/003000 A1 | 1/2006 |
| WO | WO-2006/005627 A1 | 1/2006 |
| WO | WO-2006/008069 A1 | 1/2006 |
| WO | WO-2006/048268 A1 | 5/2006 |
| WO | WO-2006/058737 A1 | 6/2006 |
| WO | WO-2006/061181 A1 | 6/2006 |
| WO | WO-2006/061182 A1 | 6/2006 |
| WO | WO-2006/073054 A1 | 7/2006 |
| WO | WO-2006/081973 A1 | 8/2006 |
| WO | WO-2006/098080 A1 | 9/2006 |
| WO | WO-2006/100896 A1 | 9/2006 |
| WO | WO-2006/117052 A1 | 11/2006 |
| WO | WO-2006/122630 A1 | 11/2006 |
| WO | WO-2007/006807 A1 | 1/2007 |
| WO | WO-2007/017066 A1 | 2/2007 |
| WO | WO-2007/063754 A1 | 6/2007 |
| WO | WO-2007/065549 A1 | 6/2007 |
| WO | WO-2007/065678 A1 | 6/2007 |
| WO | WO-2007/068325 A1 | 6/2007 |
| WO | WO-2007/115610 A1 | 10/2007 |
| WO | WO-2007/137725 A1 | 12/2007 |
| WO | WO-2007/140847 A1 | 12/2007 |
| WO | WO-2008/006449 A1 | 1/2008 |
| WO | WO-2008/056746 A1 | 5/2008 |
| WO | WO-2008/083975 A1 | 7/2008 |
| WO | WO-2008/086851 A1 | 7/2008 |
| WO | WO-2008/145239 A2 | 12/2008 |
| WO | WO-2009/062578 A1 | 5/2009 |
| WO | WO-2009/141026 A1 | 11/2009 |
| WO | WO-2009/146770 A2 | 12/2009 |
| WO | WO-2010/006680 A1 | 1/2010 |
| WO | WO-2010/012330 A1 | 2/2010 |
| WO | WO-2010/015306 A1 | 2/2010 |

OTHER PUBLICATIONS

Hasegawa, M., et al., "Excitation energy transfer between $D_{3h}$ melamines and Pr(III) in the solid state," Science and Technology of Advanced Materials (2006), vol. 7, pp. 72-76.

(56) References Cited

OTHER PUBLICATIONS

Horvath-Bordon, E., et al., "Alkalicyamelurates, $M_3|C_6N_7O_3|\cdot xH_2O$, M=Li, Na, K, Rb, Cs: UV-luminescent and thermally very stable ionic tri-s-triazine derivatives," Dalton Trans. (2004), pp. 3900-3908.

Ishii, A., et al., Novel emission properties of melem caused by the heavy metal effect of lanthanides(III) in a LB film, Photochem. Photobiol. Sci. (2007), vol. 6, pp. 804-809.

Lotsch, B.V., et al., "New Light on an Old Story: Formation of Melam during Thermal Condensation of Melamine," Chem. Eur. J. (2007), vol. 13, pp. 4956-4968.

Schroeder, H., et al., "Some Reactions of Cyameluric Chloride," Journal of Organic Chemistry (1962), vol. 27, pp. 4262-4266.

Traber, B., et al., "Donor-Substituted Heptaazaphenalene as a Non-linear Optically Active Molecule with Multiple Charge-Transfer Transitions," Eur. J. Org. Chem. (2004), pp. 4387-4390.

Windgassen, Jr., R.J., et al., "Cyclazines. A New Class of Aromatic Heterocycles," Journal of the American Chemical Society (1959), pp. 1459-1465.

First Office Action issued in corresponding JP Application No. 2011-550439, mailed Dec. 3, 2013.

Tagami, K., et al., "Interface Sensitivity in Quantum Transport through Single Molecules", Nano Letters, 2004, vol. 4, No. 2, pp. 209-212.

* cited by examiner

ORGANIC ELECTRONIC DEVICE

CROSS-REFERENCE TO RELATED APPLICATIONS

This application is a national stage application (under 35 U.S.C. §371) of PCT/EP2010/000330, filed Jan. 20, 2010, which claims benefit of German application 10 2009 009 227.3, filed Feb. 17, 2009.

BACKGROUND OF THE INVENTION

The present invention relates to organic electronic devices, in particular organic electroluminescent devices, which comprise aromatic nitrogen heterocyclic compounds.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. However, further improvements are still desirable before these devices can be used for high-quality and long-lived displays. Thus, there is currently still a need for improvement, in particular, in the lifetime, the efficiency and the operating voltage of organic electroluminescent devices. Furthermore, it is necessary for the compounds to have high thermal stability and to be sublimable without decomposition.

Improvements are still desirable, in particular, in the charge-injection and -transport materials since it is precisely the properties of the charge-transport materials that also have a significant influence on the above-mentioned properties of the organic electroluminescent device. In particular, there is a need for improvement in electron-transport materials and hole-injection or hole-transport materials which simultaneously result in good efficiency, a long lifetime and a low operating voltage. The properties of these materials, in particular, are frequently also limiting for the lifetime, the efficiency and the operating voltage of the organic electroluminescent device.

AlQ$_3$ has already been used for some time as electron-transport material (for example U.S. Pat. No. 4,539,507), but has a number of disadvantages: it cannot be vapour-deposited without a residue since it partially decomposes at the sublimation temperature, which represents a major problem, in particular, for production plants. This has the consequence that the vapour-deposition sources must repeatedly be cleaned or changed. Furthermore, decomposition products of AlQ$_3$ reach the OLED, where they contribute to a shortened lifetime and reduced quantum and power efficiency. In addition, AlQ$_3$ has low electron mobility, which results in higher voltages and thus in lower power efficiency. In order to avoid short circuits in the display, it would be desirable to increase the layer thickness; this is not possible with AlQ$_3$ owing to the low charge-carrier mobility and the resultant increase in voltage. The charge-carrier mobility of other electron conductors (U.S. Pat. No. 4,539,507) is likewise too low to build up thicker layers therewith, with the lifetime of the OLED being even worse than on use of AlQ$_3$. The inherent colour (yellow in the solid state) of AlQ$_3$ also proves to be unfavourable, possibly resulting in colour shifts due to reabsorption and weak re-emission, especially in the case of blue OLEDs. Blue OLEDs can only be produced here with considerable adverse effects on efficiency and colour location.

Apart from various triarylamine derivatives or carbazole derivatives, the hole-injection or hole-transport materials used in organic electroluminescent devices in accordance with the prior art are, in particular, also hexaazatriphenylene derivatives, in particular those which are substituted by cyano groups (for example WO 01/049806). There likewise still continues to be a need for improvement here in respect of the lifetime, the efficiency and the operating voltage.

Thus, there continues to be a demand for electron-transport materials and hole-injection and hole-transport materials which result in good efficiencies and at the same time in long lifetimes in organic electroluminescent devices. Surprisingly, it has now been found that organic electroluminescent devices which comprise certain nitrogen heteroaromatic compounds—indicated below—as electron-transport materials or as hole-injection or hole-transport materials have significant improvements over the prior art. Using these materials, it is possible simultaneously to obtain high efficiencies and long lifetimes.

Heptaazaphenalene derivatives, in particular those which are substituted by aromatic groups, alkoxy groups or amino groups, are already known in the literature as protection against UV radiation (for example WO 07/006807) or flame-proofing agents (for example WO 01/021698). Use of such compounds in organic electronic devices is not known.

BRIEF SUMMARY OF THE INVENTION

The invention thus relates to an organic electronic device comprising a cathode, an anode and at least one organic layer, which is arranged between the cathode and anode and which comprises at least one compound of the formula (1) or formula (2):

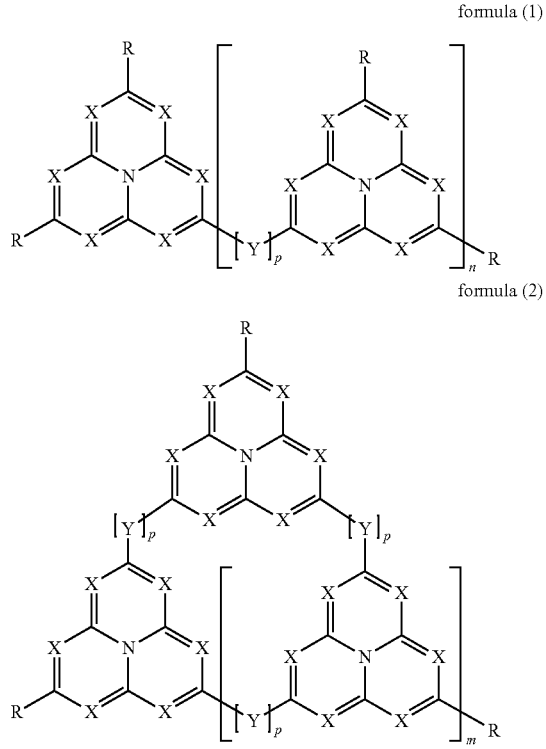

where the following applies to the symbols and indices used:

X is on each occurrence, identically or differently, CR$^1$ or N;

Y is on each occurrence, identically or differently, a divalent group selected from the group consisting of B(R$^1$)$_2$, C(R$^1$)$_2$, NR$^1$, O, S, C(=O), C=C(R$^1$)$_2$, S(=O), S(=O)$_2$, P(=O)(R$^1$)$_2$, or a divalent aromatic or heteroaromatic ring system having 5 to 18 aromatic ring atoms, which may be substituted by one or more radicals R$^1$;

R is on each occurrence, identically or differently, H, D, F, Cl, Br, I, CHO, N(R$^1$)$_2$, N(Ar)$_2$, C(=O)Ar, P(=O)(Ar)$_2$, S(=O)Ar, S(=O)$_2$Ar, CR$^1$=CR$^1$Ar, CN, NO$_2$, Si(R$^1$)$_3$, B(OR$^1$)$_2$, B(R$^1$)$_2$, B(Ar)$_2$, B(N(R$^1$)$_2$)$_2$, OSO$_2$R$^1$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thio-alkoxy group having 3 to 40 C atoms, each of which may be substituted by one or more radicals R$^1$, where one or more non-adjacent CH$_2$ groups may be replaced by R$^1$C=CR$^1$, C≡C, Si(R$^1$)$_2$, Ge(R$^1$)$_2$, Sn(R$^1$)$_2$, C=O, C=S, C=Se, C=NR$^1$, P(=O)(R$^1$), SO, SO$_2$, NR$^1$, O, S or CONR$^1$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^1$, or an aryloxy or heteroaryloxy group having 5 to 60 aromatic ring atoms, which may in each case be substituted by one or more radicals R$^1$, or a combination of these systems;

R$^1$ is on each occurrence, identically or differently, H, D, F, Cl, Br, I, CHO, N(R$^2$)$_2$, N(Ar)$_2$, C(=O)Ar, P(=O)(Ar)$_2$, S(=O)Ar, S(=O)$_2$Ar, CR$^2$=CR$^2$Ar, CN, NO$_2$, Si(R$^2$)$_3$, B(OR$^2$)$_2$, B(R$^2$)$_2$, B(N(R$^2$)$_2$)$_2$, OSO$_2$R$^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thio-alkoxy group having 3 to 40 C atoms, each of which may be substituted by one or more radicals R$^2$, where one or more non-adjacent CH$_2$ groups may be replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy or heteroaryloxy group having 5 to 60 aromatic ring atoms, which may be substituted by one or more radicals R$^2$, or a combination of these systems;

Ar is on each occurrence, identically or differently, an aromatic or heteroaromatic ring system having 5 to 30 aromatic ring atoms, which may be substituted by one or more non-aromatic radicals R$^1$; two radicals Ar which are bonded to the same nitrogen or phosphorus atom may also be linked to one another here by a single bond or a bridge selected from B(R$^2$), C(R$^2$)$_2$, Si(R$^2$)$_2$, C=O, C=NR$^2$, C=C(R$^2$)$_2$, O, S, S=O, SO$_2$, N(R$^2$), P(R$^2$) and P(=O)R$^2$;

R$^2$ is on each occurrence, identically or differently, H, D or an aliphatic, aromatic and/or heteroaromatic hydrocarbon radical having 1 to 20 C atoms, in which, in addition, H atoms may be replaced by F; two or more adjacent substituents R$^2$ here may also form a mono- or polycyclic, aliphatic or aromatic ring system with one another;

n is 0, 1, 2, 3, 4, 5 or 6;
m is 0, 1, 2 or 3;
p is on each occurrence, identically or differently, 0, 1, 2 or 3, where p=0 means that a single bond is present between the units.

A DETAILED DESCRIPTION OF THE INVENTION

For the purposes of the present invention, an organic electronic device is taken to mean a device which comprises an anode and a cathode and at least one layer arranged between the anode and cathode, where this layer comprises at least one organic or organometallic compound. However, it is not necessary for the device to comprise only organic layers. For example, it is also possible for one or more layers which comprise inorganic materials or consist completely of inorganic materials to be present. Likewise, the anode and cathode may consist of or comprise purely inorganic materials.

The organic electronic device is selected, in particular, from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and "organic plasmon emitting devices" (D. M. Koller et al., *Nature Photonics* 2008, 1-4), but in particular organic electroluminescent devices (OLEDs).

For the purposes of this invention, an aryl group contains 6 to 60 C atoms; for the purposes of this invention, a heteroaryl group contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, pyrene, quinoline, isoquinoline, etc.

For the purposes of this invention, an aromatic ring system contains 6 to 60 C atoms in the ring system. For the purposes of this invention, a heteroaromatic ring system contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be interrupted by a short non-aromatic unit (preferably less than 10% of the atoms other than H), such as, for example, an sp$^3$-hybridised C, N or O atom. Thus, for example, systems such as 9,9'-spirobifluorene, 9,9-diarylfluorene, triarylamine, diaryl ether, stilbene, benzophenone, etc., are also intended to be taken to be aromatic ring systems for the purposes of this invention. An aromatic or heteroaromatic ring system is likewise taken to mean systems in which a plurality of aryl or heteroaryl groups are linked to one another by single bonds, for example biphenyl, terphenyl or bipyridine.

For the purposes of the present invention, a C$_1$- to C$_{40}$-alkyl group, in which, in addition, individual H atoms or CH$_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl and 2,2,2-trifluoroethyl. For the purposes of this invention, an alkenyl group is taken to mean, in particular, ethenyl, propenyl, butenyl, pentenyl, cyclopentenyl, hexenyl, cyclohexenyl, heptenyl, cycloheptenyl, octenyl and cyclooctenyl. For the purposes of this invention, an alkynyl group is taken to mean, in particular, ethynyl, propynyl, butynyl, pentynyl, hexynyl, heptynyl or octynyl. A $C_1$- to $C_{40}$-alkoxy group is particularly preferably taken to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may also in each case be substituted by the above-mentioned radicals R and which may be linked to the aromatic or heteroaromatic ring system via any desired positions, is taken to mean, in particular, groups derived from benzene, naphthalene, anthracene, phenanthrene, benzanthracene, benzophenanthrene, pyrene, chrysene, perylene, fluoroanthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

The compounds of the formula (1) or formula (2) preferably have a glass transition temperature $T_G$ of greater than 70° C., particularly preferably greater than 100° C., very particularly preferably greater than 110° C.

In a preferred embodiment of the invention, all symbols X in compounds of the formula (1) or of the formula (2) stand for N, or all symbols X stand for $CR^1$. Preference is thus given to the compounds of the formula (3), formula (4), formula (5) or formula (6):

formula (3)

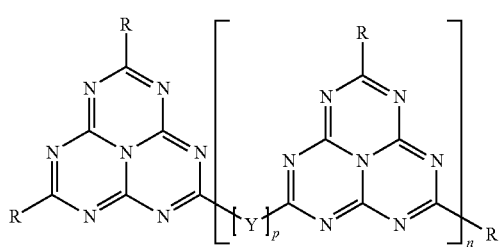

where the symbols and indices used have the same meaning as described above. $R^1$ in formula (4) and formula (6) particularly preferably stands for hydrogen or deuterium, in particular for hydrogen. Very particular preference is given to the compounds of the formula (3).

In a preferred embodiment of the invention, the index n in compounds of the formulae (1), (3) and (4) stands for 0, 1 or 2, particularly preferably for 0 or 1, very particularly preferably for 0.

In a further preferred embodiment of the invention, the index m in compounds of the formulae (2), (5) and (6) stands for 0, 1 or 2, particularly preferably for 1.

In a further preferred embodiment of the invention, the index p in the formulae (1), (3) and (4) stands, identically or differently on each occurrence, for 0 or 1, and in the formulae (2), (5) and (6) stands, identically or differently on each occurrence, for 1 or 2.

In a preferred embodiment of the invention, R in the compounds of the formulae (1) to (6) stands, identically or differently on each occurrence, for F, $N(R^1)_2$, $N(Ar)_2$, $C(=O)Ar$, $P(=O)(Ar)_2$, CN, $NO_2$, a straight-chain alkyl group having 1 to 10 C atoms or a branched or cyclic alkyl group having 3 to 10 C atoms, each of which may be substituted by one or more radicals $R^1$, where one or more H atoms may be replaced by F or CN, or an aromatic or heteroaromatic ring system having 5 to 40 aromatic ring atoms, which may in each case be substituted by one or more radicals $R^1$. In a particularly preferred embodiment of the invention, R in the compounds of the formulae (1) to (6) stands, identically or differently on each occurrence, for F, CN, $CF_3$ or an aromatic or heteroaromatic ring system having 5 to 30 aromatic ring atoms, which may in each case be substituted by one or more radicals $R^1$, but is preferably unsubstituted. Particularly preferred aromatic or heteroaromatic ring systems which can form the group R are selected from the group consisting of phenyl, 2-, 3- or 4-pyridyl, pyrazinyl, 2-, 4- or 5-pyrimidinyl, 3- or 4-pyridazinyl, ortho-, meta- or para-biphenyl, ortho-, meta- or para-terphenyl, 2-fluorenyl, 2-spirobifluorenyl, 1-naphthyl, 2-naphthyl, anthracenyl, phenylanthracenyl, 1- or 2-naphthylanthracenyl, binaphthyl, pyrenyl, fluoranthenyl, 2-, 3-, 4-, 5-, 6- or 7-benzanthracenyl, N-imidazolyl, N-benzimidazolyl, phenyl-N-benzimidazolyl, N-phenylbenzimidazolyl, phenyl-N-phenylbenzimidazolyl, or combinations of these groups, each of which may be substituted by one or more radicals $R^1$.

It is particularly preferred for all radicals R to be selected identically. This applies, in particular, to the preferred and particularly preferred radicals R mentioned above. This preference is due to the better synthetic accessibility of the compounds.

Particular preference is given to the structures of the formulae (1) to (6) given above in which n=0 or 1, in particular n=0, and m=1, and in which R has the preferred or particularly preferred meaning mentioned above and in which p has the preferred meaning mentioned above.

Preference is furthermore given to the structures of the formulae (1) to (6) given above in which Y, if p is not equal to 0, stands, identically or differently on each occurrence, for a divalent group selected from the group consisting of $C(R^1)_2$, $NR^1$ and a divalent aryl or heteroaryl group having 5 to 14 aromatic ring atoms, which may be substituted by one or more radicals $R^1$. Y in the formulae (1), (3) and (4) is particularly preferably, identically or differently on each occurrence, selected from a single bond, $NR^1$ or a divalent aryl or heteroaryl group having 5 to 10 aromatic ring atoms, which may be substituted by one or more radicals $R^1$. Y in the formulae (2), (5) and (6) is particularly preferably, identically or differently on each occurrence, $NR^1$.

Examples of preferred compounds of the formulae (1) to (6) are structures (1) to (90) depicted below.

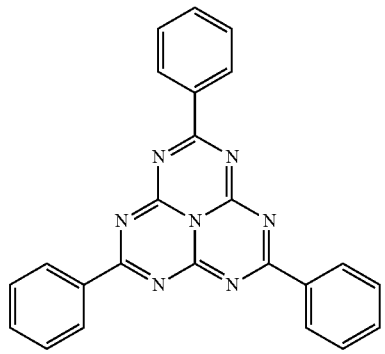
(1)

-continued

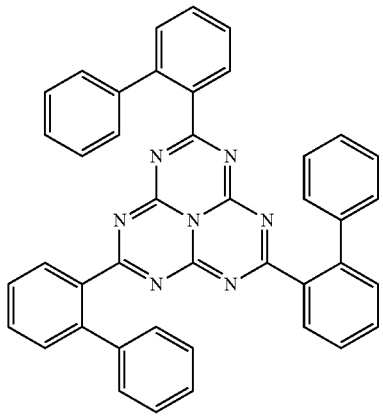
(2)

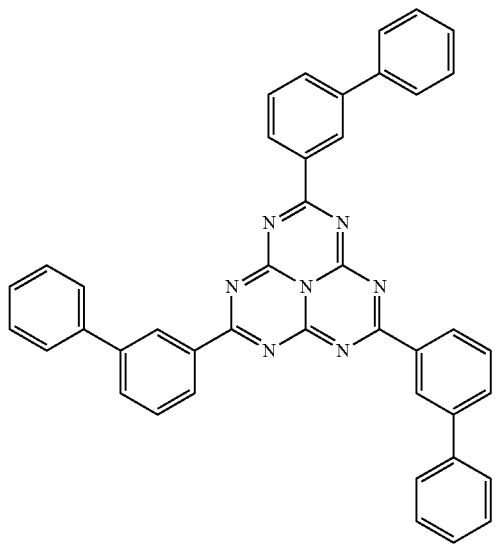
(3)

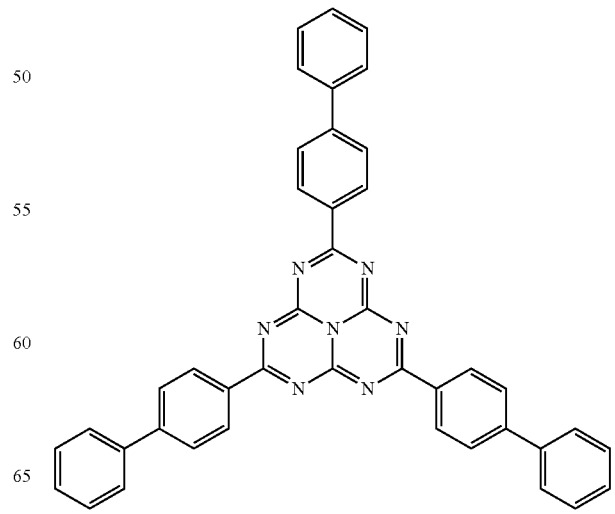
(4)

(5)
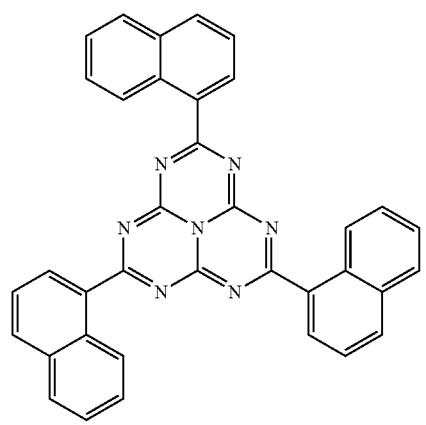
(6)
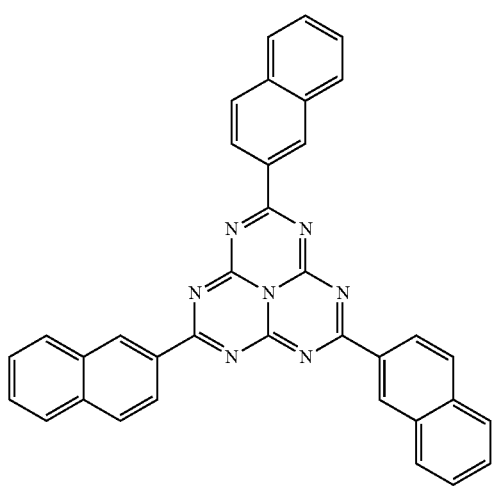
(7)
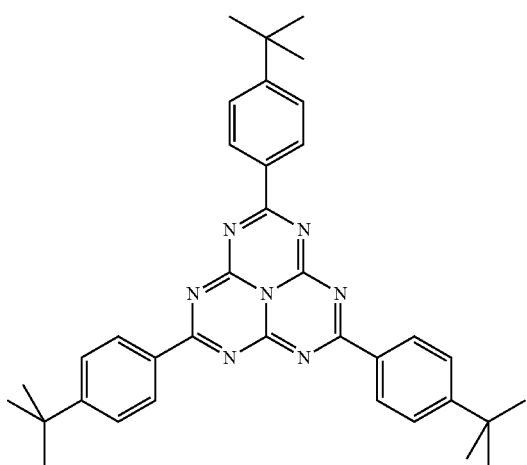
(8)
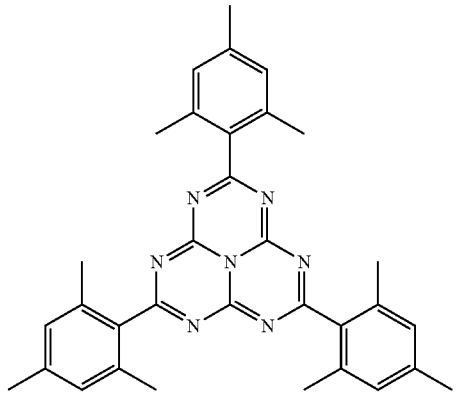
(9)
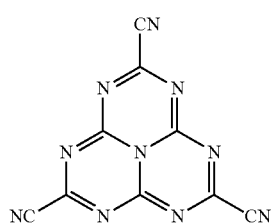
(10)
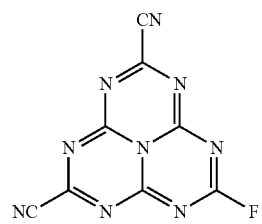
(11)
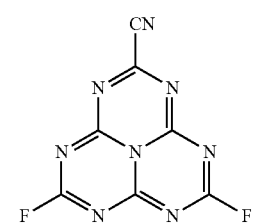
(12)
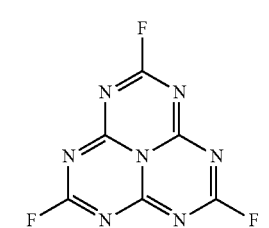
(13)
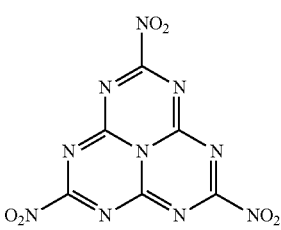

(14)
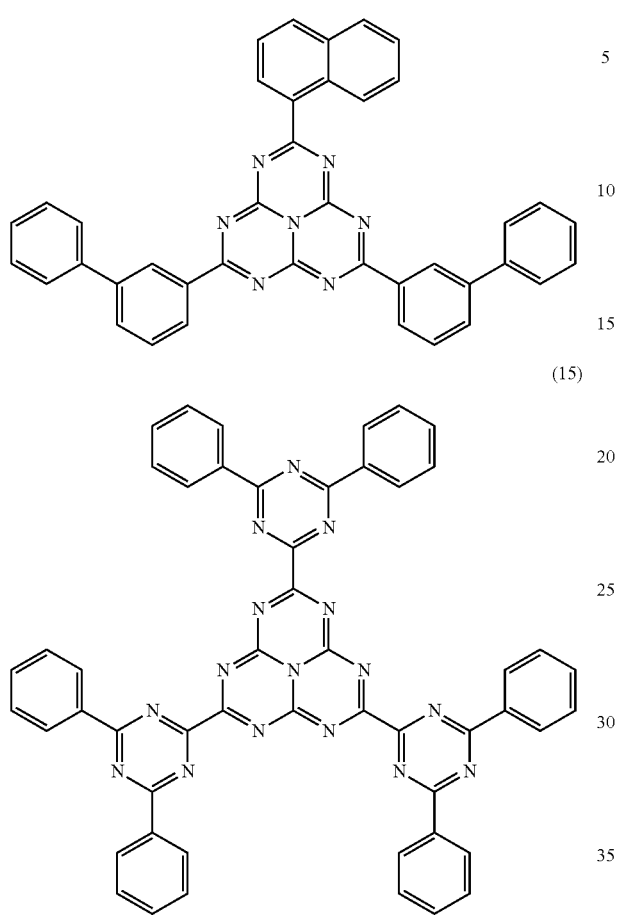
(15)
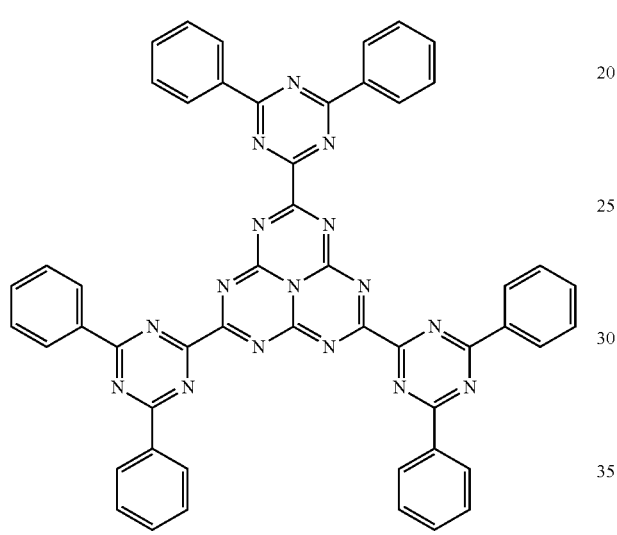
(16)
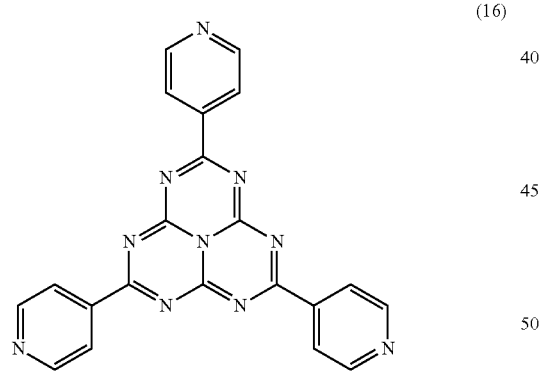
(17)
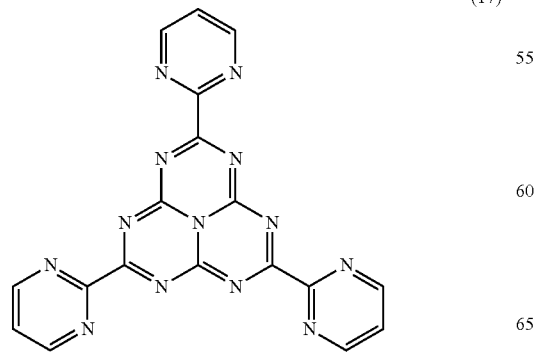
(18)
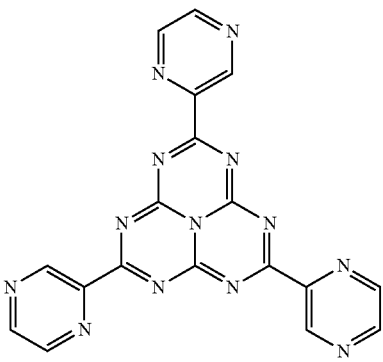
(19)
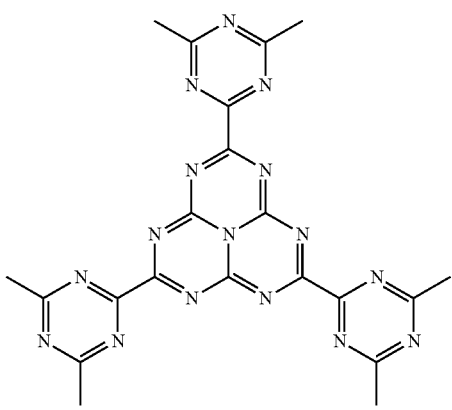
(20)
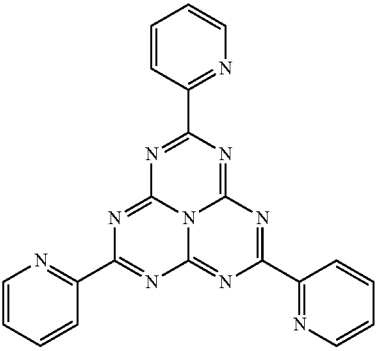
(21)
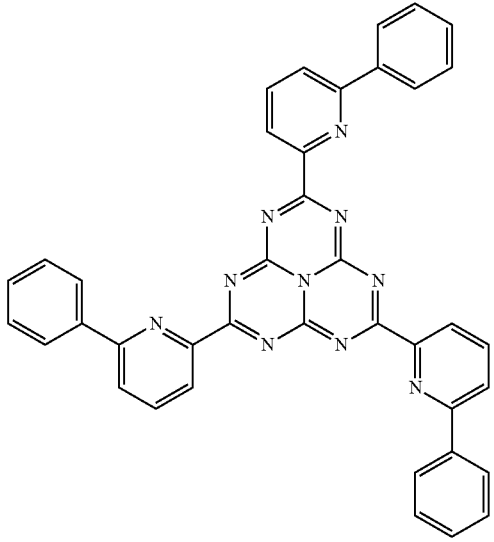

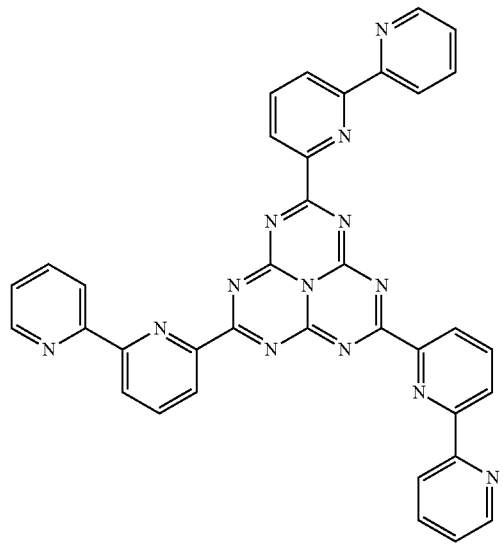
(22)
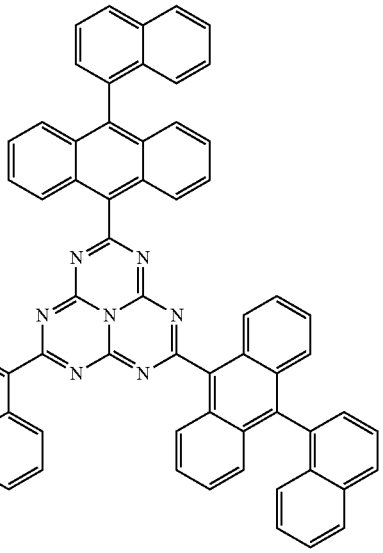
(25)
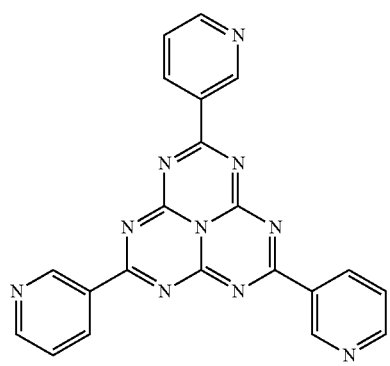
(23)
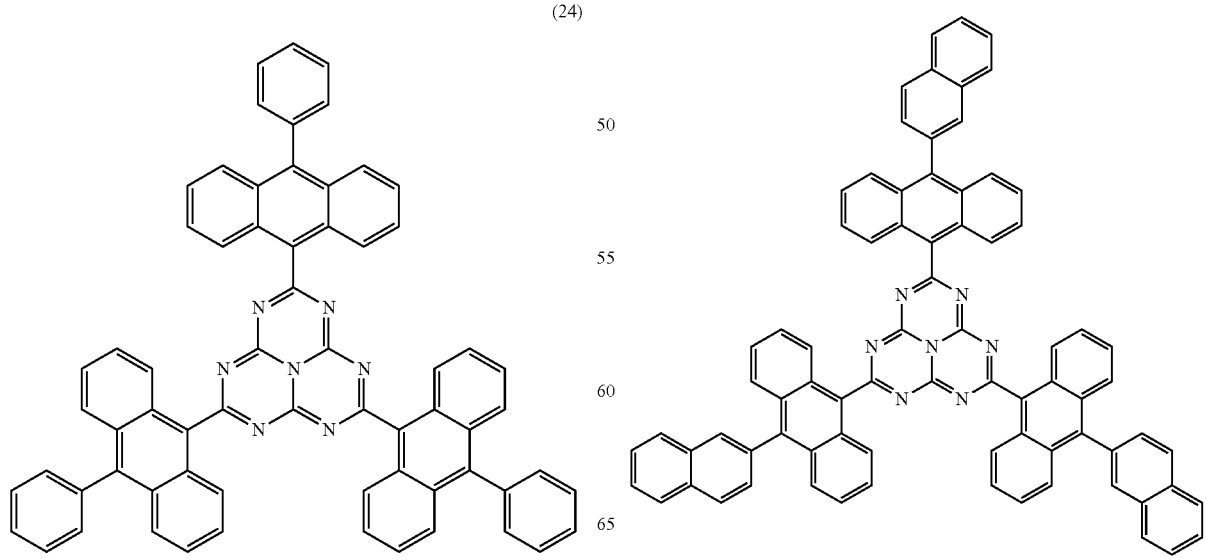

(27)
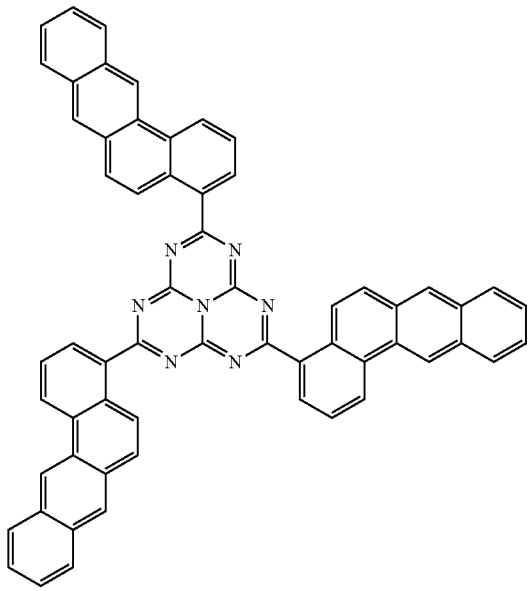
(28)
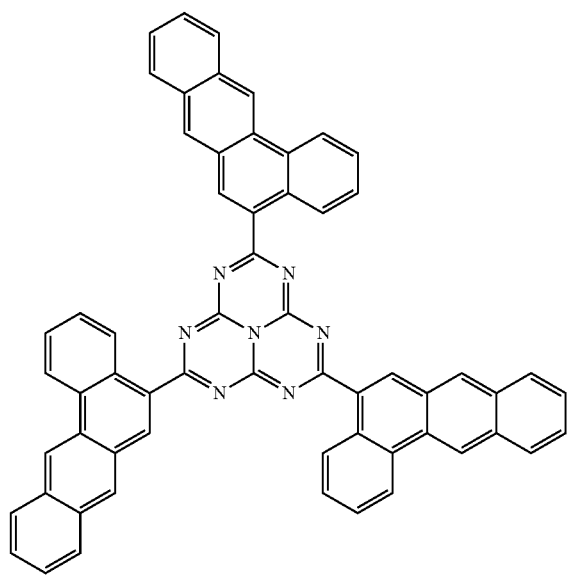
(29)
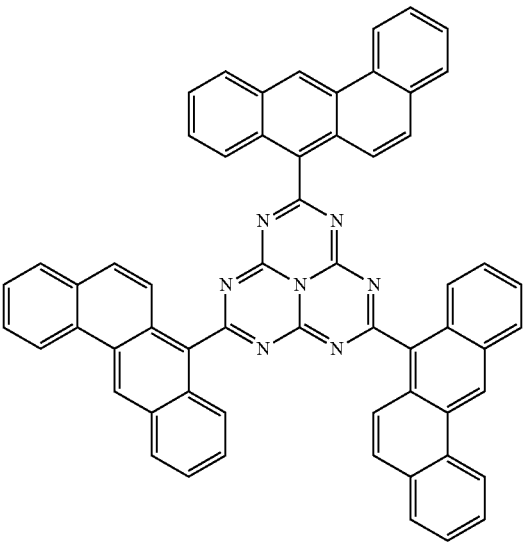
(30)
(31)
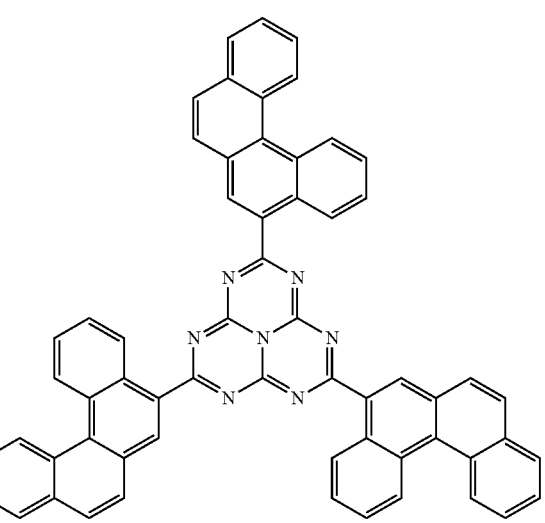

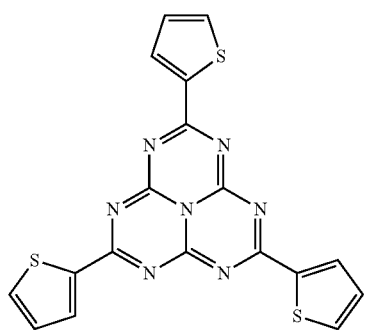
(32)
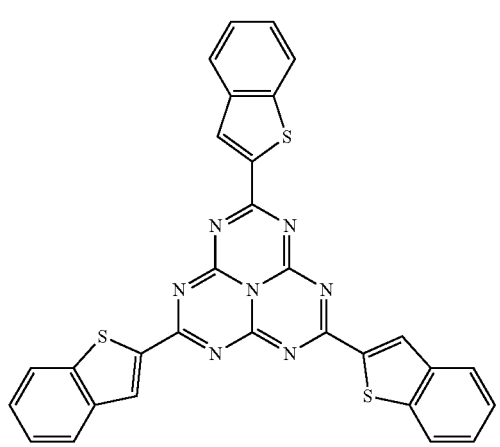
(33)
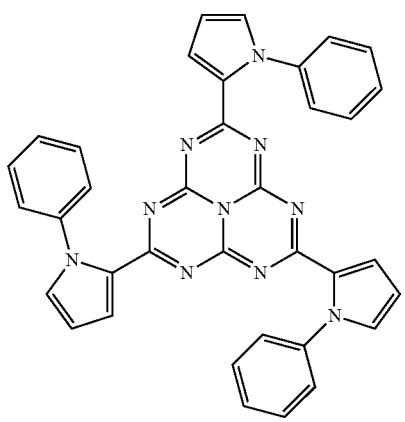
(34)
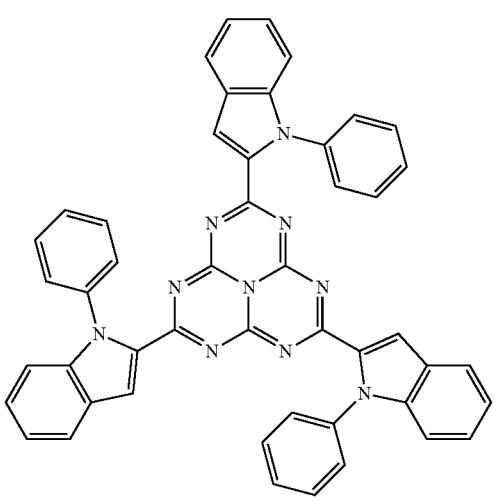
(35)
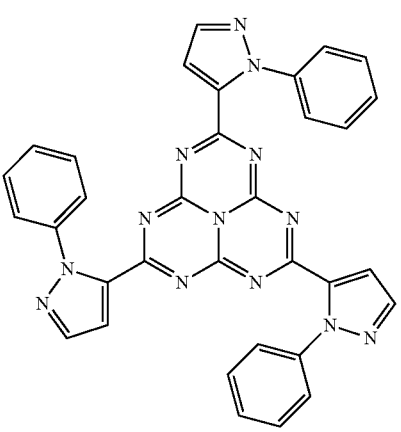
(36)
(37)

(38) 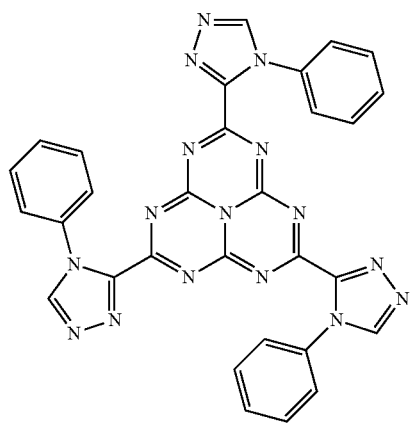
(39) 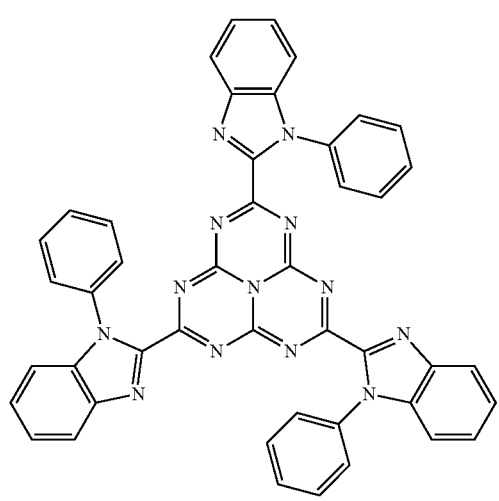
(40) 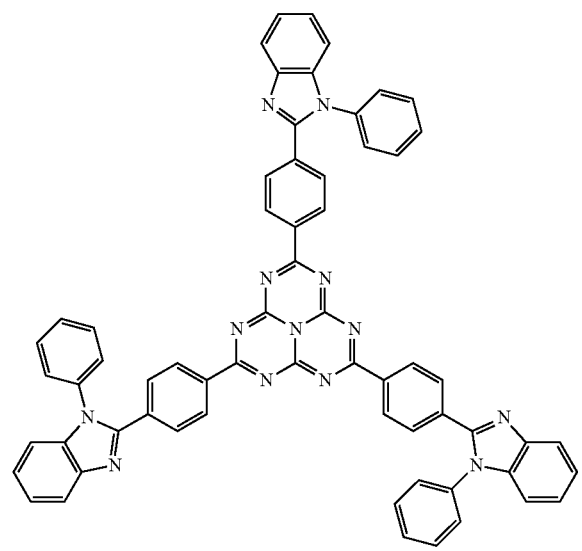
(41) 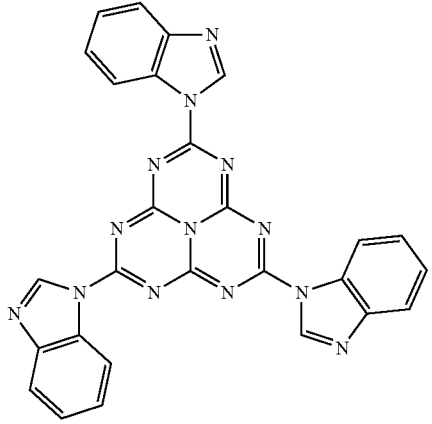
(42) 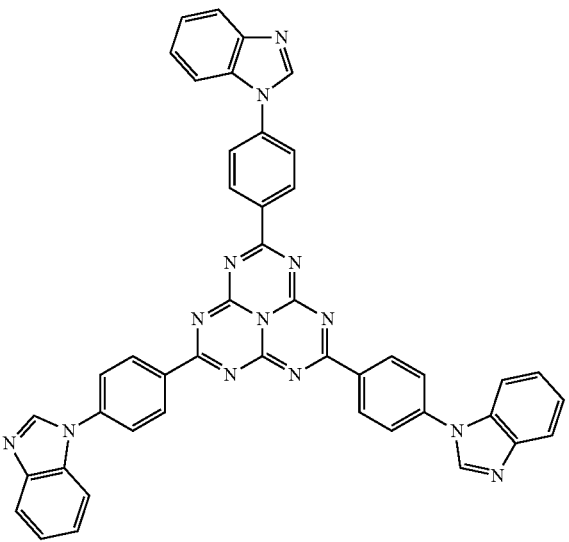
(43) 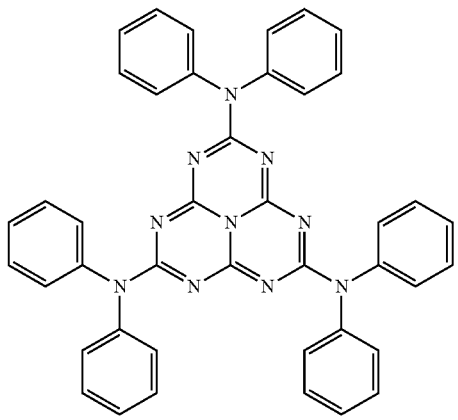

(44)
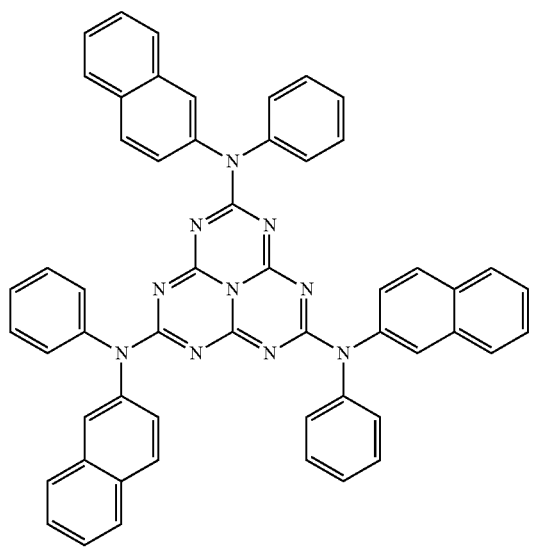
(45)
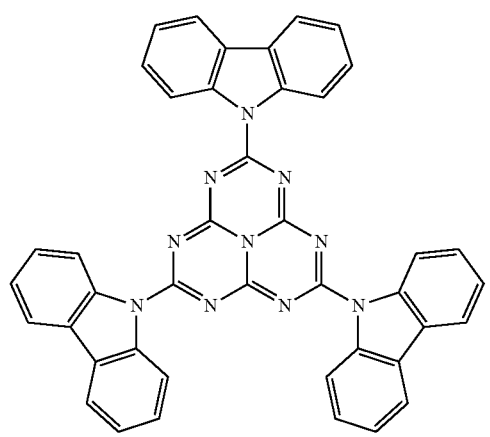
(46)
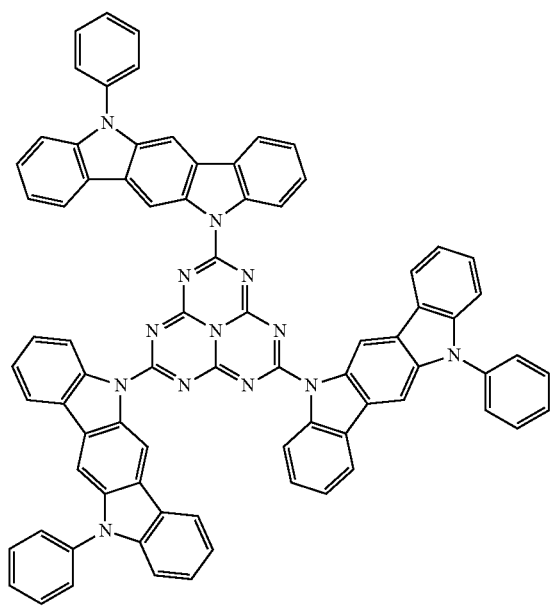
(47)
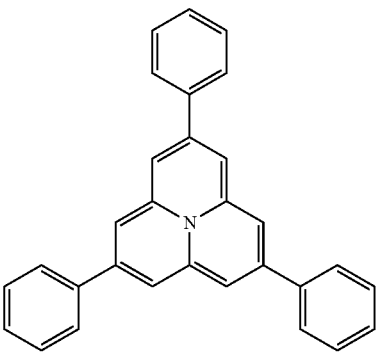
(48)
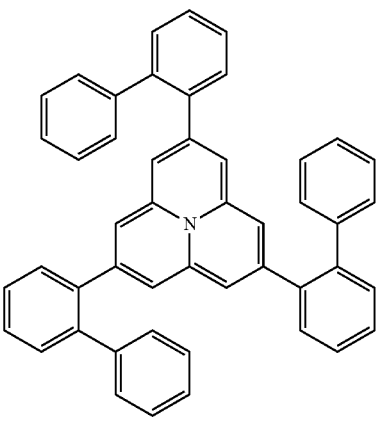
(49)
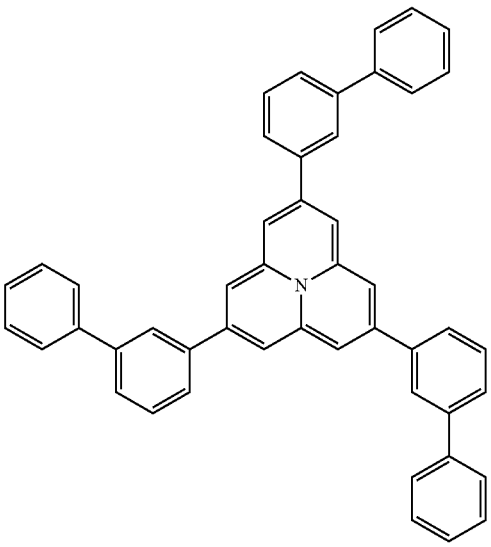

(50)
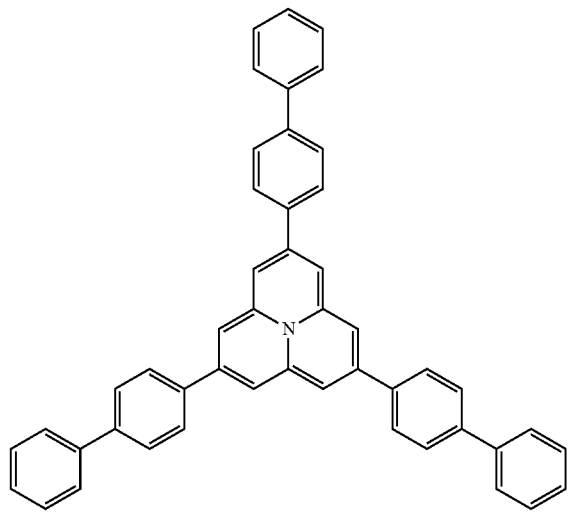
(51)
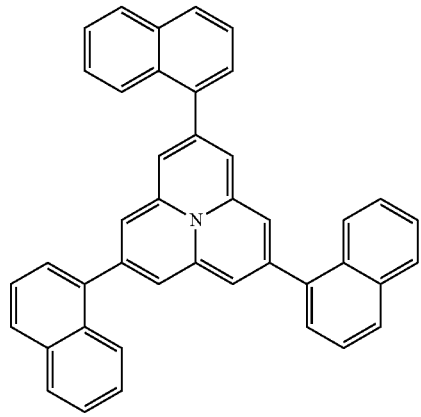
(52)
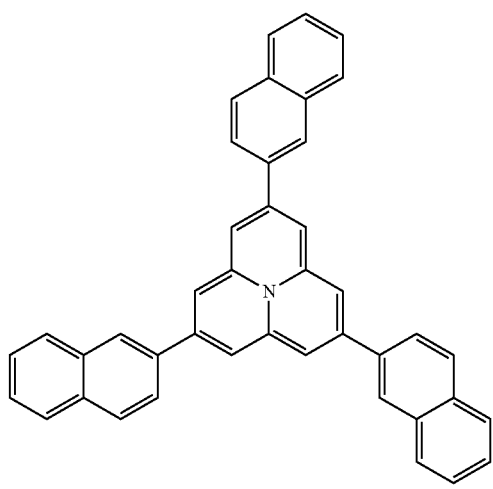
(53)
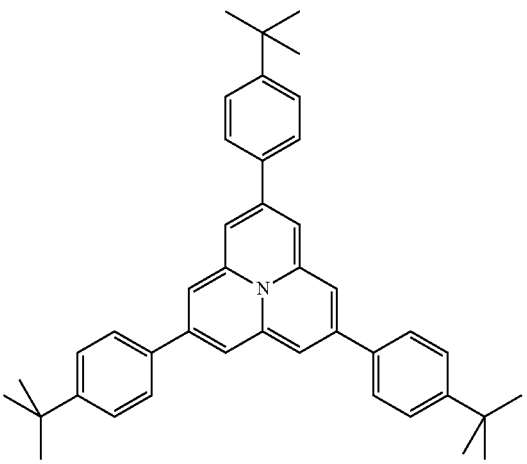
(54)
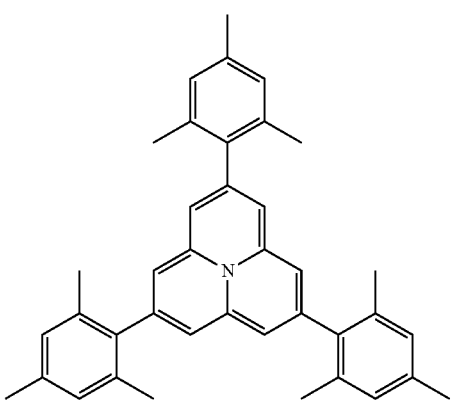
(55)
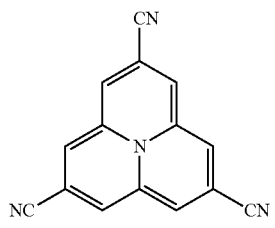
(56)
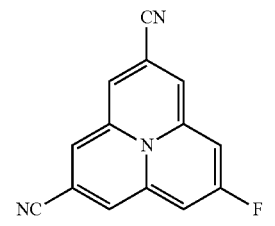
(57)
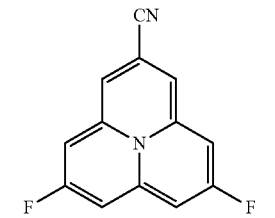

-continued
(58)
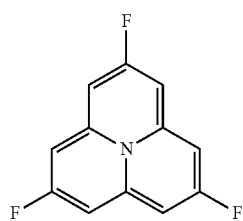
(59)
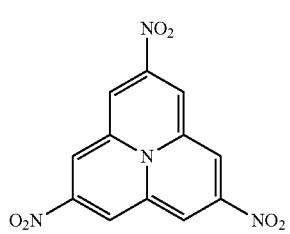
(60)
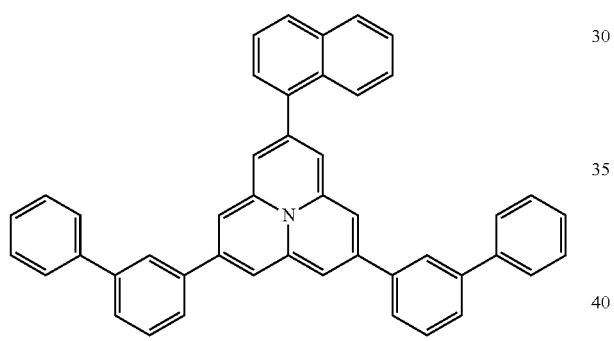
(61)
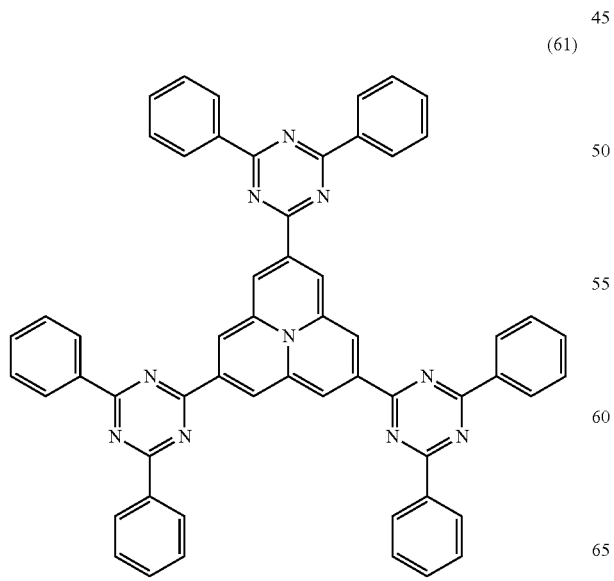
-continued
(62)
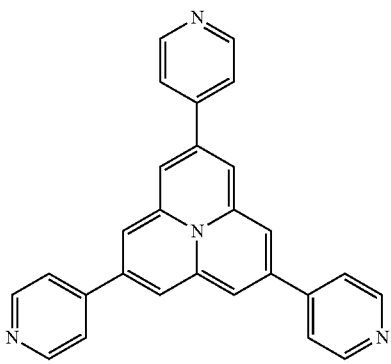
(63)
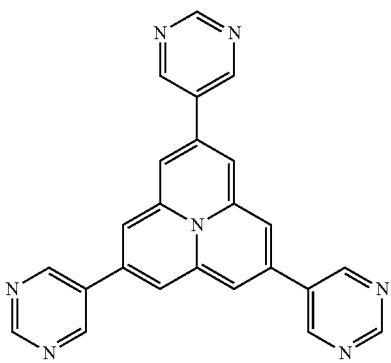
(64)
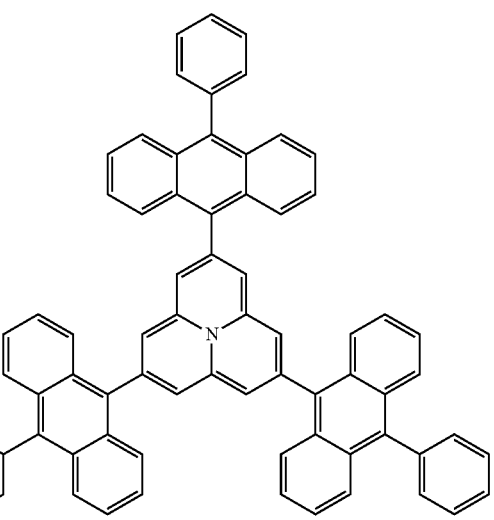

(65)
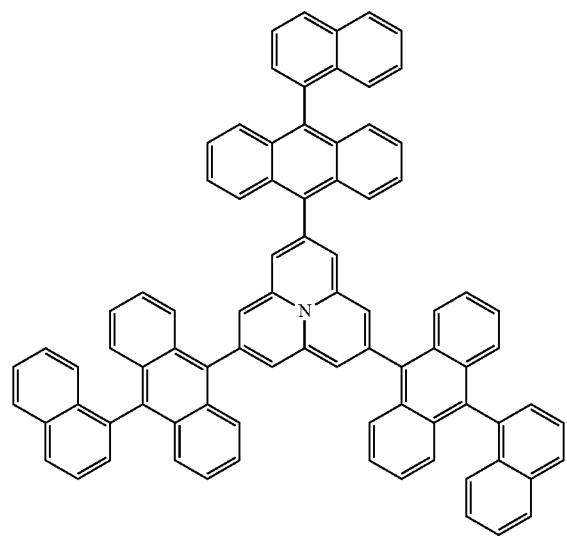
(67)
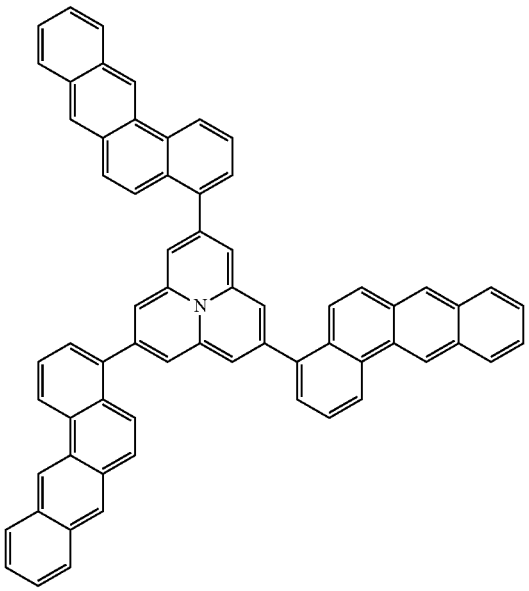
(66)
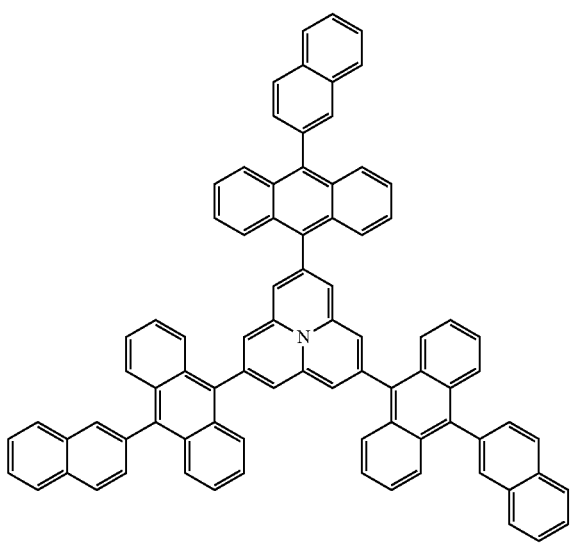
(68)
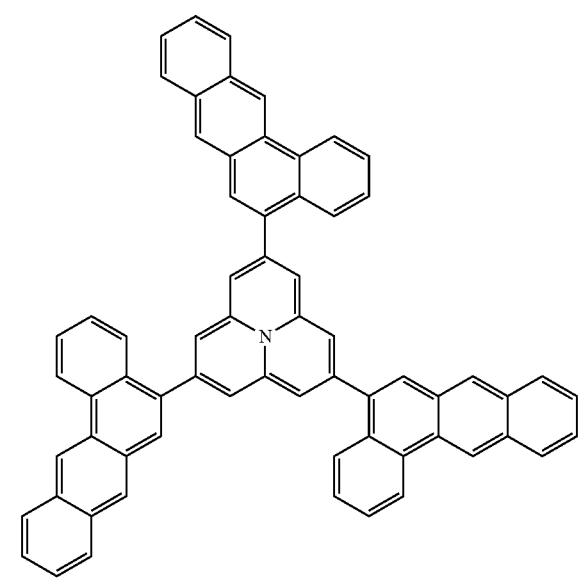

(69)
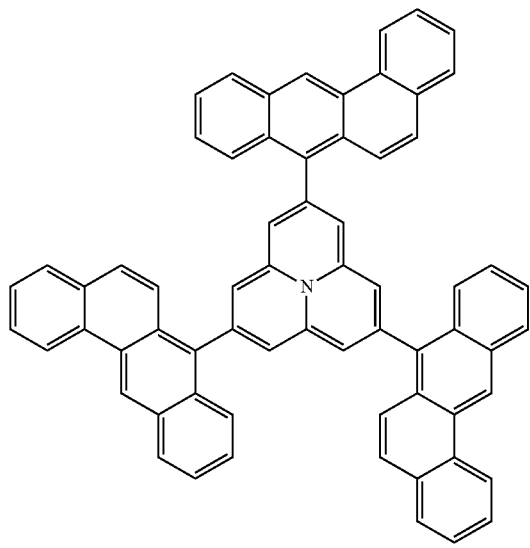
(70)
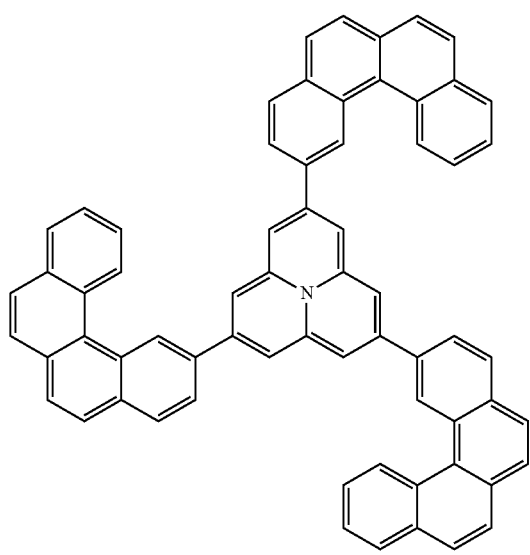
(71)
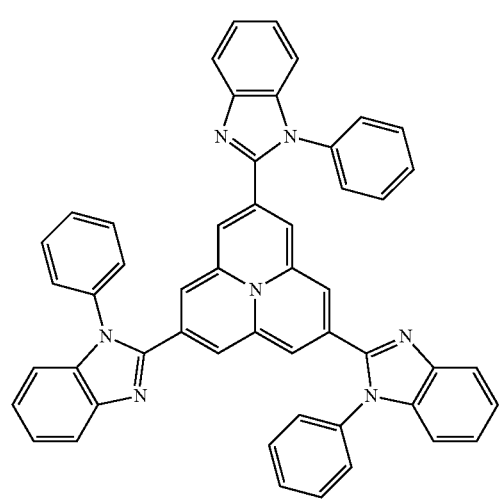
(72)
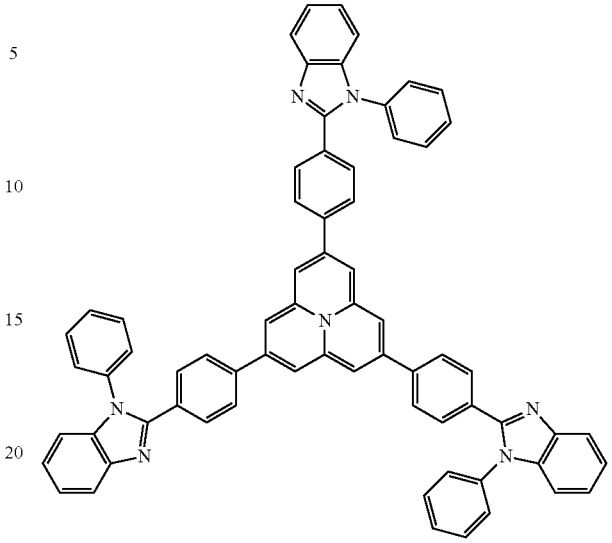
(73)
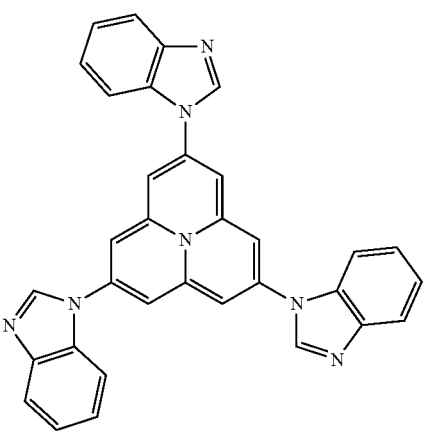
(74)
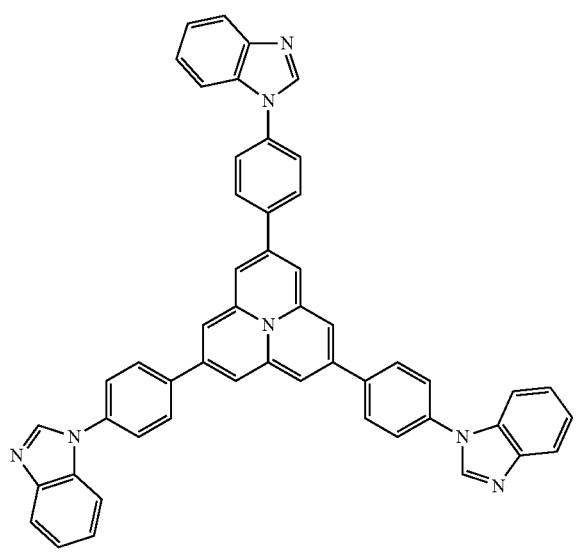

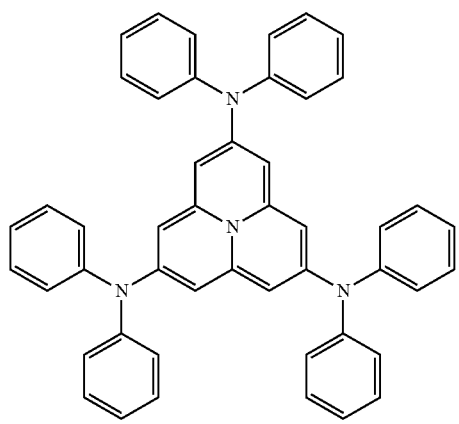
(75)
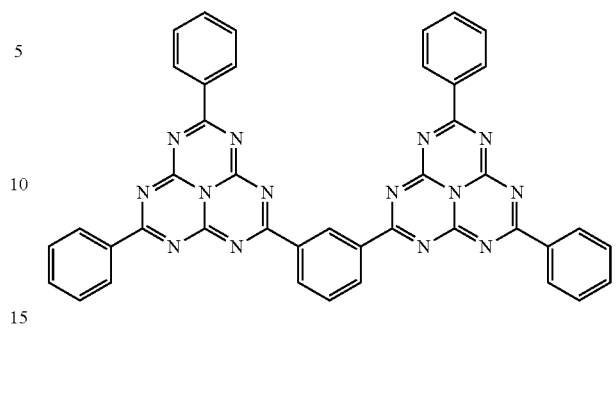
(78)
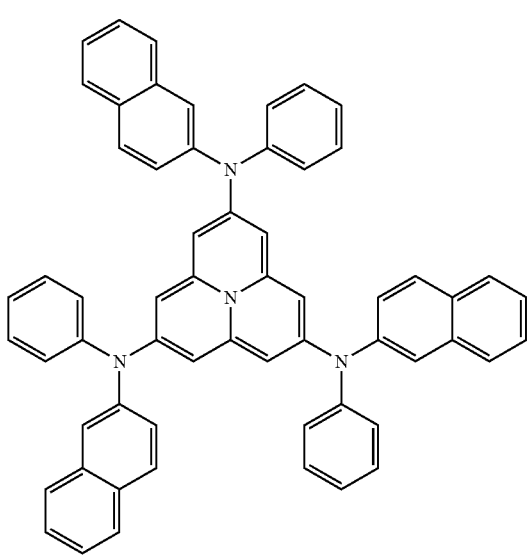
(76)
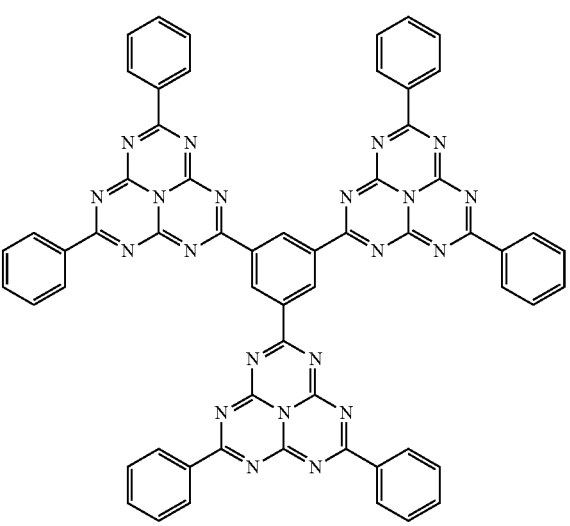
(79)
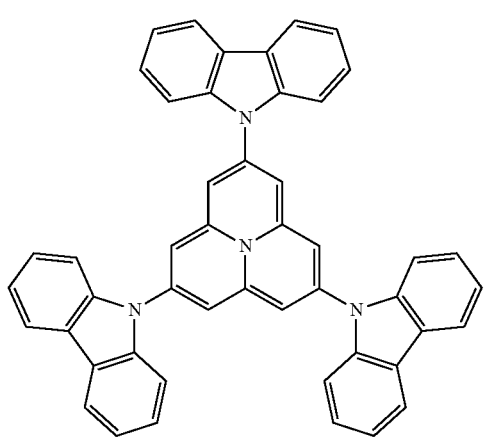
(77)
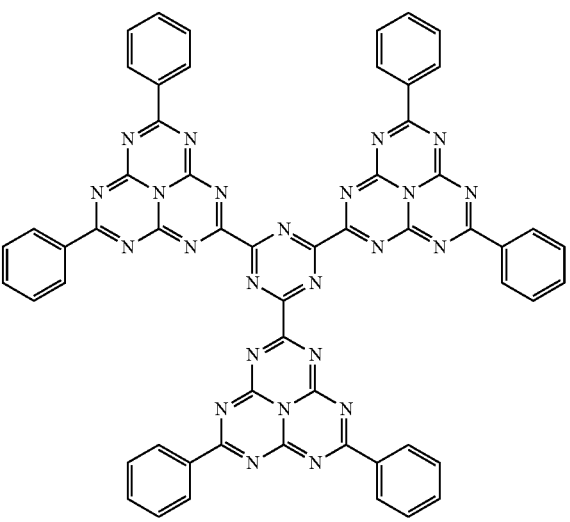
(80)

(81)
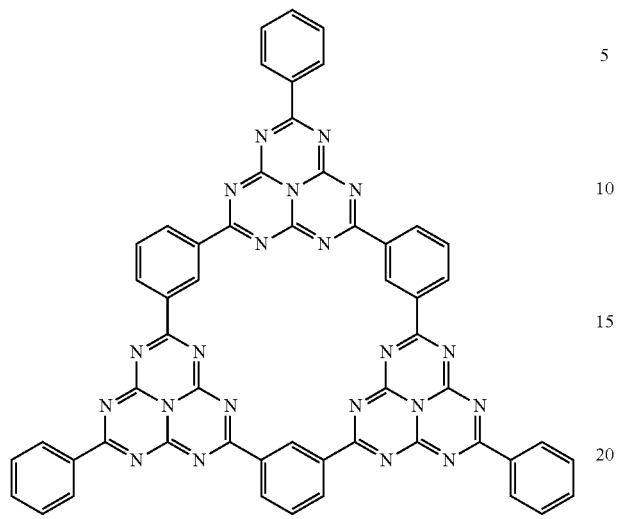
(82)
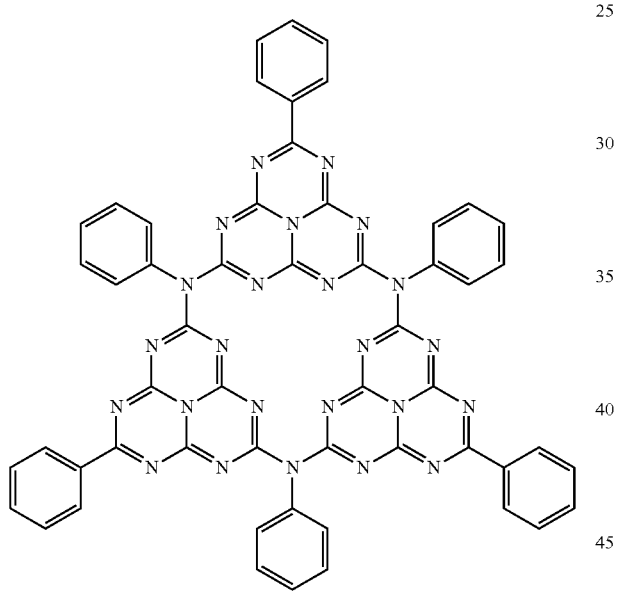
(83)
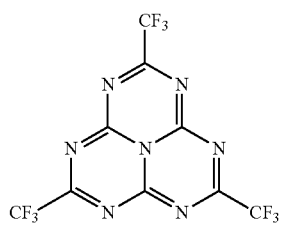
(84)
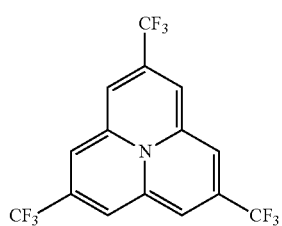
(85)
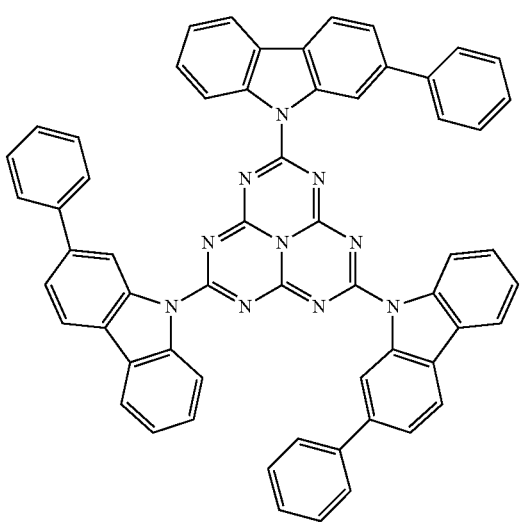
(86)
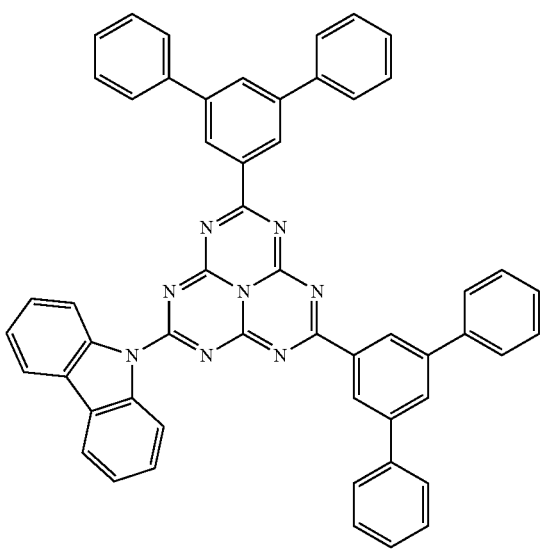
(87)
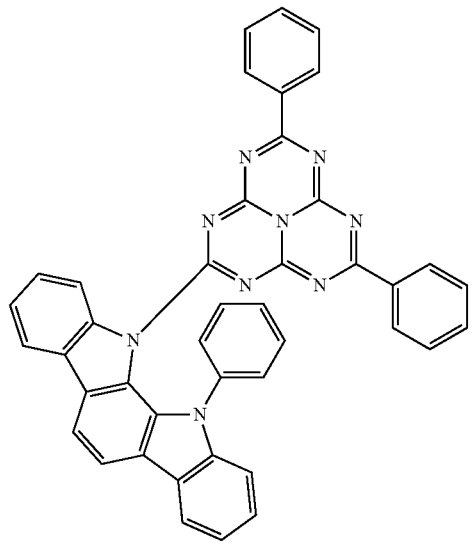

(88)

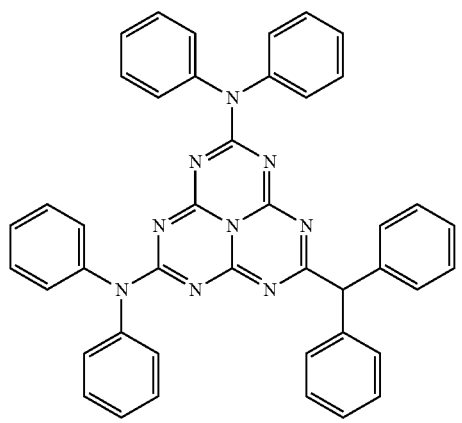

(89)

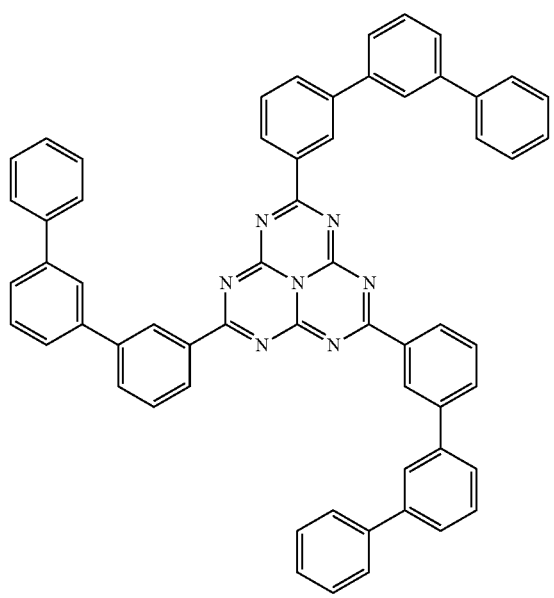

(90)

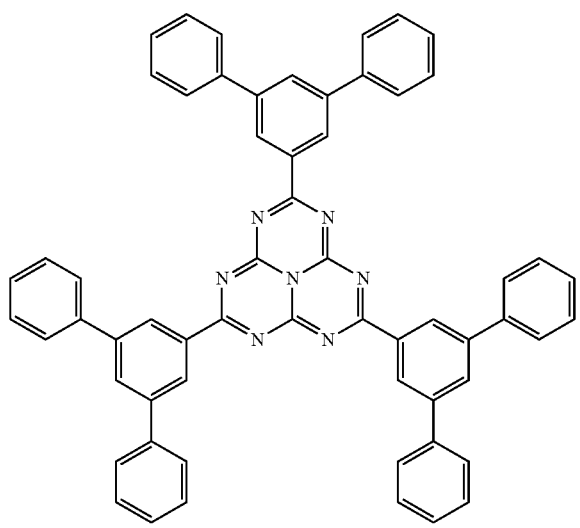

The synthesis of the compounds of the formulae (1) to (6) is known to the person skilled in the art of organic chemistry. The starting compound used in all cases can be trihaloheptaazaphenalene or a corresponding phenalene derivative containing fewer nitrogen atoms. Trichloroheptaazaphenalene is particularly suitable. This can be obtained by direct chlorination of the corresponding acid, for example in accordance with EP 1854797. This can furthermore be obtained by a Sandmeyer reaction, i.e. by diazotisation, of triaminoheptaazaphenalene, which is in turn accessible directly from melamine (for example in accordance with H. May, *J. Applied Chemistry* 1959, 9, 340-344). The chlorine substituents can then be replaced by other nucleophiles, for example F or CN, by nucleophilic aromatic substitution, in particular with activation by a Lewis acid. The introduction of other groups, for example substituted amino groups, is also possible in this way. Furthermore, the introduction of aromatic substituents by a Friedel-Crafts reaction is possible. The introduction of aromatic or heteroaromatic substituents is likewise possible by reaction of trichloroheptaazaphenalene with organometallic derivatives of aromatic or heteroaromatic compounds, in particular with organolithium compounds or Grignard compounds. Furthermore, palladium-catalysed coupling reactions, in particular with boronic acid derivatives (Suzuki coupling) or organozinc compounds (Negishi coupling), for the introduction of aromatic substituents are possible. Diarylamino groups can be introduced by palladium-catalysed Hartwig-Buchwald coupling. The halogen function can be converted, by transmetallation using organolithium compounds or Grignard compounds, into an electrophilic group, which can then be coupled to a multiplicity of electrophiles, such as, for example, arylboron halides, aldehydes, ketones, nitriles, esters, halo esters, carbon dioxide, arylphosphine halides, halosulfinic acids, haloarylsulfonic acids, etc. The trinitro compound is accessible by oxidation of triaminoheptaazaphenalene. Asymmetrically substituted compounds can in each case be obtained by adaptation of the stoichiometry. These reactions are shown diagrammatically in scheme 1 below.

Scheme 1:

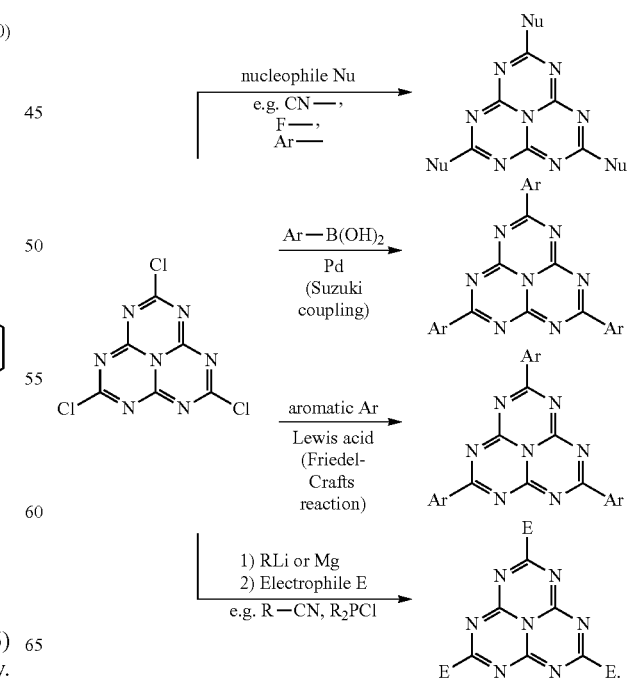

Furthermore, the corresponding triamino compound can serve as starting compound. Thus, the amino groups can be converted into nitro groups by oxidation. Furthermore, the amino groups can be substituted, for example by a Hartwig-Buchwald reaction.

Cyclic compounds of the formula (2) where Y=NH are accessible by heating 2,6,10-triaminoheptaazaphenalene at 450 to 600° C. for 15 to 60 minutes (for example in accordance with SU 1747448 A1). These can be functionalised further as described above for the non-cyclic compounds.

The reactions mentioned above are known in general terms to the person skilled in the art of organic chemistry and can also be applied by him, without inventive step, to the compounds of the formulae (1) to (6).

The compounds of the formulae (1) to (6) described above, in particular compounds in which at least one group R stands for a reactive leaving group, such as bromine, iodine, triflate, tosylate, boronic acid or boronic acid ester, can also be used as monomers for the preparation of corresponding oligomers, polymers or as the core of dendrimers, where these oligomers, polymers and dendrimers are in turn suitable for use in organic electronic devices, in particular in organic electroluminescent devices. The oligomerisation or polymerisation here is preferably carried out via the halogen functionality or the boronic acid functionality. For the purposes of this invention, an oligomer is taken to mean a compound which has about 3 to 9 recurring units. For the purposes of this invention, a polymer has about 10 or more recurring units.

The invention therefore furthermore relates to organic electronic devices, in particular organic electroluminescent devices, comprising at least one oligomer, polymer or dendrimer which comprises one or more compounds of the formulae (1) to (6), where one or more radicals R represent bonds from the compound of the formulae (1) to (6) to the polymer, oligomer or dendrimer. The polymers, oligomers or dendrimers may be conjugated, partially conjugated or non-conjugated. The oligomers or polymers may be linear or branched. In the structures linked in a linear manner, the units of the formulae (1) to (6) may be either linked directly to one another or linked to one another via a divalent group, such as, for example, via a group Y or via a substituted or unsubstituted alkylene group, via a heteroatom or via a divalent aromatic or heteroaromatic group. In branched structures, for example, three or more units of the formulae (1) to (6) may be linked via a trivalent or polyvalent group, for example via a trivalent or polyvalent aromatic or heteroaromatic group, to form a branched oligomer or polymer. The units of the formulae (1) to (6) are furthermore also particularly suitable as branching point in oligomers, polymers and dendrimers, since the tri-chloro-substituted units in particular are readily accessible synthetically.

For the preparation of the oligomers or polymers, the corresponding monomers are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or WO 07/017066) or also a plurality of these units. The polymers, oligomers and dendrimers usually also comprise further units, for example emitting (fluorescent or phosphorescent) units, such as, for example, vinyltriarylamines (for example in accordance with WO 07/068325) or phosphorescent metal complexes (for example in accordance with WO 06/003000), and/or charge-transport units. The recurring units according to the invention are particularly suitable as charge-transport units for electrons.

The invention furthermore relates to the use of compounds of the formula (1), (2), (3), (4), (5) or (6) or corresponding oligomers, polymers or dendrimers in organic electronic devices, in particular in organic electroluminescent devices.

The organic electroluminescent device comprises an anode, a cathode and at least one emitting layer, where at least one organic layer, which may be the emitting layer or another layer, comprises at least one compound of the formulae (1) to (6) or a corresponding oligomer, polymer or dendrimer.

Apart from the cathode, anode and emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, charge-generation layers and/or organic or inorganic p/n junctions. Furthermore, the layers, in particular the charge-transport layers, may also be doped. Doping of the layers may be advantageous for improved charge transport. However, it should be pointed out that each of these layers does not necessarily have to be present, and the choice of layers is always dependant on the compounds used and in particular also on whether the electroluminescent device is fluorescent or phosphorescent.

In an embodiment of the invention, the organic electroluminescent device comprises a plurality of emitting layers, where at least one organic layer, which may be an emitting layer or another layer, comprises at least one compound of one of formulae (1) to (6). These emission layers particularly preferably have in total a plurality of emission maxima between 380 nm and 750 nm, resulting overall in white emission, i.e. various emitting compounds which are able to fluoresce or phosphoresce and emit blue and yellow, orange or red light are used in the emitting layers. Particular preference is given to three-layer systems, i.e. systems having three emitting layers, where at least one of these layers comprises at least one compound of one of formulae (1) to (6) and where the three layers exhibit blue, green and orange or red emission (for the basic structure see, for example, WO 05/011013). Emitters which have broad-band emission bands and thus exhibit white emission are likewise suitable for white emission.

In a preferred embodiment of the invention, the compounds of the formulae (1) to (6) are used as hole-injection or hole-transport material. This applies, in particular, if at least one substituent R, preferably at least two substituents R, particularly preferably all three substituents R, stand for an electron-deficient group. In contrast to triarylamine derivatives, which are usually used in the hole-injection or hole-transport layer and in which hole transport takes place via the HOMO (highest occupied molecular orbital) of the corresponding compound, hole transport in compounds of the formulae (1) to (6) does not take place via the HOMO, but instead via the LUMO (lowest unoccupied molecular orbital). Particularly preferred substituents R are then selected from the group consisting of CN, F, $NO_2$, $CF_3$ and substituted or unsubstituted electron-deficient heterocycles. The electron-deficient heterocycles here are preferably selected from pyridine, pyrazine, pyrimidine, pyridazine, triazine, pyrrole, imidazole, triazole, benzimidazole, quinoline, isoquinoline, quinoxaline, thiadiazole, thiazole or oxadiazole, each of which may be substituted by one or more radicals $R^1$. Since the LUMO of these compounds is as low or even lower compared with the hexaazatriphenylene derivatives used as hole-injection materials in accordance with the prior art, the compounds of the formulae (1) to (6) are just as suitable or better as hole-injection or hole-transport materials than the materials in accordance with the prior art. For the purposes of this invention, a hole-injection material is intended to be taken to mean a compound which is employed in a hole-injection layer. For the purposes of this invention, a hole-injection layer is a layer which is directly adjacent to the anode. In the structure of the organic electroluminescent device, the hole-injection layer is usually followed by a hole-transport layer, so that the hole-injection layer is located between the anode and a hole-transport layer. For the purposes of the present invention, a hole-transport layer is a layer which is located between a hole-injection layer and the emitting layer.

In a preferred embodiment of the invention, the electroluminescent device according to the invention has a structure comprising, in this sequence: anode—hole-injection layer comprising at least one compound of one of formulae (1) to (6)—hole-transport layer, preferably comprising at least one triarylamine derivative—emitting layer—cathode. It is likewise possible in this structure to use two or more hole-transport layers, which preferably all comprise at least one triarylamine derivative. A further preferred structure of the electroluminescent device comprises, in this sequence: anode—hole-injection layer, preferably comprising at least one triarylamine derivative—hole-transport layer comprising at least one compound of one of formulae (1) to (6)—hole-transport layer, preferably comprising at least one triarylamine derivative—emitting layer—cathode. It is likewise possible in this structure for a further hole-transport layer, preferably comprising at least one triarylamine derivative, to be introduced between the hole-injection layer and the layer comprising the compound of one of formulae (1) to (6) and/or for two or more hole-transport layers, which preferably each comprise at least one triarylamine derivative, to be used instead of a hole-transport layer, which preferably comprises a triarylamine derivative, between the layer comprising the compound of one of formulae (1) to (6) and the emitting layer. In addition, these devices may furthermore comprise one or more of the further layers mentioned above, for example electron-transport layers, etc.

In still a further embodiment of the invention, the compounds of the formulae (1) to (6) are employed as electron-transport material or as hole-blocking material in an electron-transport layer or hole-blocking layer. For the purposes of this invention, a hole-blocking layer is a layer which is located between an emitting layer and an electron-transport layer and is directly adjacent to the emitting layer. It is preferred here for the substituents R to stand, identically or differently on each occurrence, for an aromatic or heteroaromatic ring system, which is preferably selected from the groups mentioned above. It may furthermore be preferred for the compound to be doped with electron-donor compounds. This applies, in particular, to use in an electron-transport layer. Suitable dopants are alkali metals or alkali metal complexes or compounds, in particular lithium compounds, for example lithium quinolinate.

In still a further embodiment of the invention, the compounds of the formulae (1) to (6) are employed as charge-generation material in a charge-generation layer.

In still a further embodiment of the invention, the compounds of the formulae (1) to (6) are employed as matrix material for an emitting compound, in particular for a phosphorescent compound. This applies, in particular, to compounds in which R stands for an aryl or heteroaryl group. The phosphorescent compound here is preferably a red- or green-phosphorescent compound.

In the above-mentioned functions, i.e., in particular, as hole-injection or -transport material, as electron-transport material or as charge-generation material, the materials are also suitable for other organic electronic devices, as have been mentioned above.

The cathode of the electronic device according to the invention is preferably metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). In the case of multilayered structures, further metals which have a relatively high work function, such as, for example, Ag, can also be used in addition to the said metals, in which case combinations of the metals, such as, for example, Ca/Ag or Ba/Ag, are then generally used. Preference is likewise given to metal alloys, in particular alloys comprising an alkali metal or alkaline-earth metal and silver, particularly preferably an alloy of Mg and Ag. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, CsF, $Cs_2CO_3$, $BaF_2$, MgO, NaF, etc.). The layer thickness of this interlayer is preferably between 0.5 and 5 nm.

The anode of the electronic device according to the invention is preferably materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent in order either to facilitate irradiation of the organic material (O-SCs) or the coupling-out of light (OLEDs/PLEDs, O-lasers). A preferred structure uses a transparent anode. Preferred anode materials here are conductive mixed metal oxides. Particular preference is given to indium-tin oxide (ITO) or indium-zinc oxide (IZO). Preference is furthermore given to conductive, doped organic materials, in particular conductive, doped polymers.

The device is correspondingly (depending on the application) structured, provided with contacts and finally hermetically sealed, since the lifetime of such devices is drastically shortened in the presence of water and/or air.

In general, all further materials as employed in accordance with the prior art in organic electroluminescent devices can also be employed in combination with the compounds of the formulae (1) to (6). The emitting layer here may comprise fluorescent and/or phosphorescent dopants, preferably in each case in combination with a matrix material (host material).

Suitable fluorescent dopants are selected from the class of the monostyrylamines, the distyrylamines, the tristyrylamines, the tetrastyrylamines, the styrylphosphines, the styryl ethers and the arylamines. A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding phosphines and ethers are defined analogously to the amines. For the purposes of this invention, an arylamine or an aromatic amine is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred dopants are selected from indenofluorenamines or indenofluorenediamines, for example in accordance with WO 06/122630, benzoindenofluorenamines or benzoindenofluorenediamines, for example in accordance with WO 08/006449, and dibenzoindenofluorenamines or dibenzoindenofluorenediamines, for example in accordance with WO 07/140847. Examples of dopants from the class of the styrylamines are substituted or unsubstituted tristilbenamines or the dopants described in WO 06/000388, WO 06/058737, WO 06/000389, WO 07/065549 and WO 07/115610. Preference is furthermore given to the condensed hydrocarbons disclosed in the unpublished application DE 102008035413.9.

Further suitable fluorescent dopants are the structures depicted in the following table, and the derivatives of these structures disclosed in JP 06/001973, WO 04/047499, WO 06/098080, WO 07/065678, US 2005/0260442 and WO 04/092111.

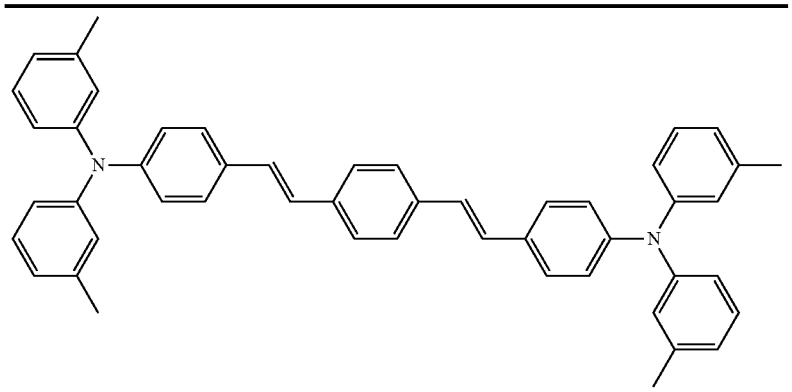

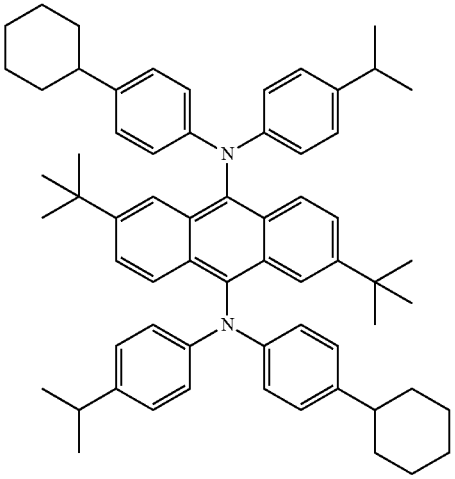 [SMILES: CC(C)c1ccc(N(c2ccc(C3CCCCC3)cc2)c2c3ccc(C(C)(C)C)cc3c(N(c3ccc(C(C)C)cc3)c3ccc(C4CCCCC4)cc3)c3ccc(C(C)(C)C)cc23)cc1]

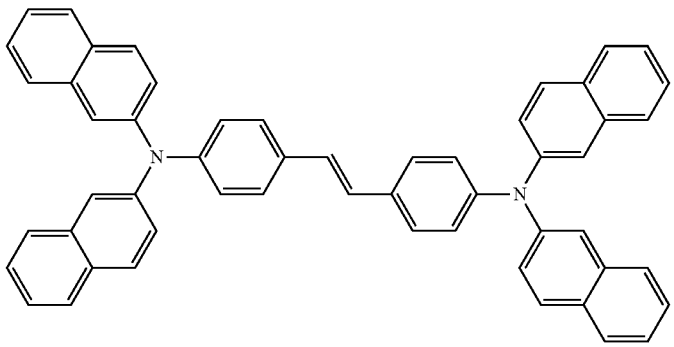 [SMILES: C(=C\c1ccc(N(c2ccc3ccccc3c2)c2ccc3ccccc3c2)cc1)/c1ccc(N(c2ccc3ccccc3c2)c2ccc3ccccc3c2)cc1]

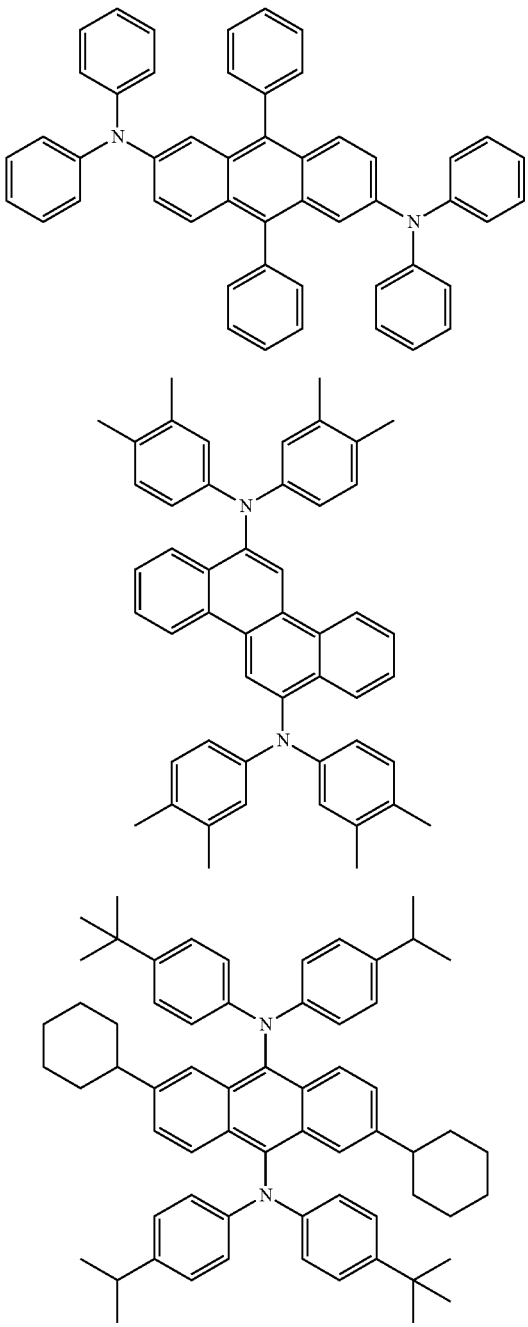

Suitable host materials for the fluorescent emitters are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052), the benzanthracenes (for example in accordance with WO 08/145239) or the benzophenanthrenes (for example in accordance with the as yet unpublished application DE 102009005746.3). Particularly preferred host materials are selected from the classes of the oligoarylenes, comprising naphthalene, anthracene, benzanthracene, benzophenanthrene and/or pyrene, or atropisomers of these compounds, the oligoarylenevinylenes, the ketones, the phosphine oxides and the sulfoxides. Very particularly preferred host materials are selected from the classes of the oligoarylenes, comprising anthracene, benzanthracene, benzophenanthrene and/or pyrene, or atropisomers of these compounds. For the purposes of this invention, an oligoarylene is intended to be taken to mean a compound in which at least three aryl or arylene groups are bonded to one another.
Suitable host materials are furthermore, for example, the materials depicted in the following table, and derivatives of these materials, as disclosed in WO 04/018587, WO 08/006449, U.S. Pat. No. 5,935,721, US 2005/0181232, JP 2000/273056, EP 681019, US 2004/0247937 and US 2005/0211958.
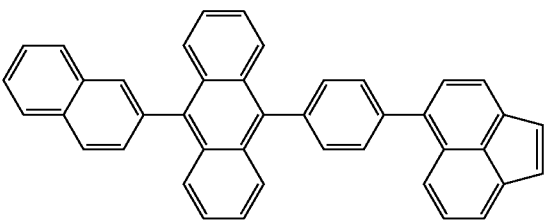
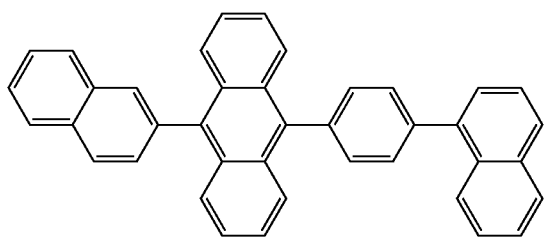 [SMILES: c1ccc2cc(-c3c4ccccc4c(-c4ccc(-c5cccc6ccccc56)cc4)c4ccccc34)ccc2c1]
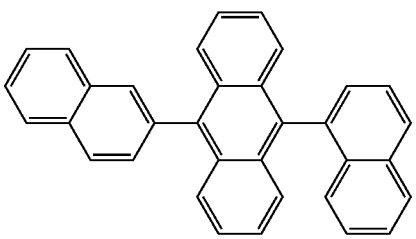
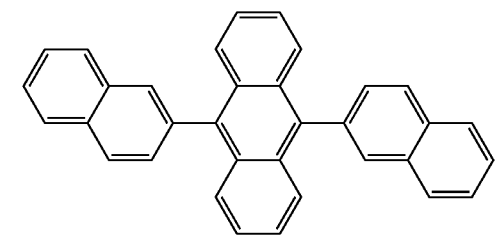 [SMILES: c1ccc2cc(-c3c4ccccc4c(-c4ccc5ccccc5c4)c4ccccc34)ccc2c1]
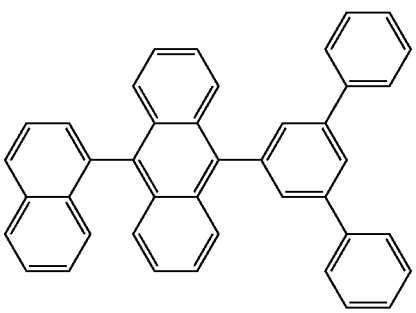 [SMILES: c1ccc(-c2cc(-c3ccccc3)cc(-c3c4ccccc4c(-c4cccc5ccccc45)c4ccccc34)c2)cc1]
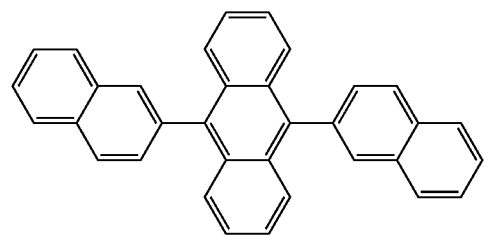
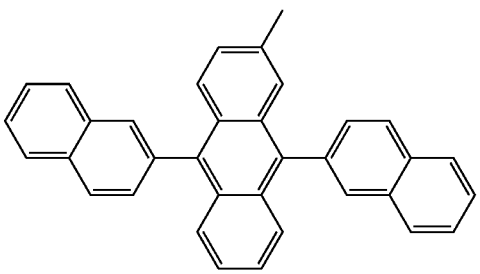 [SMILES: Cc1ccc2c(-c3ccc4ccccc4c3)c3ccccc3c(-c3ccc4ccccc4c3)c2c1]
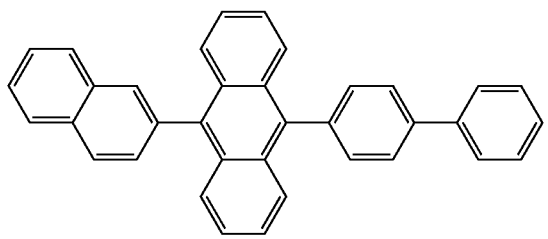
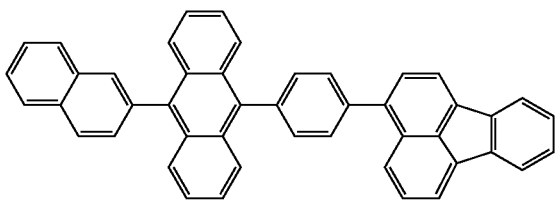 [SMILES: c1ccc2c(c1)-c1cccc3c(-c4ccc(-c5c6ccccc6c(-c6ccc7ccccc7c6)c6ccccc56)cc4)ccc-2c13]
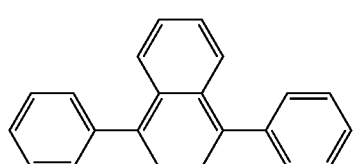
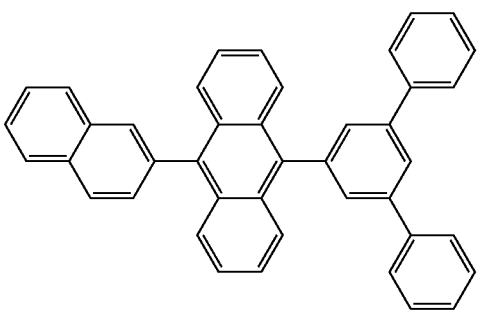 [SMILES: c1ccc(-c2cc(-c3ccccc3)cc(-c3c4ccccc4c(-c4ccc5ccccc5c4)c4ccccc34)c2)cc1]
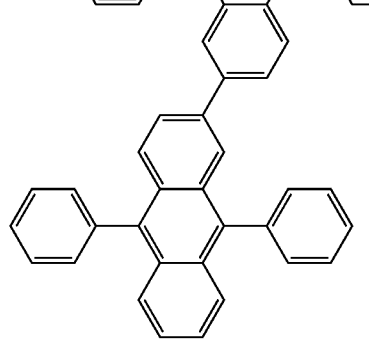

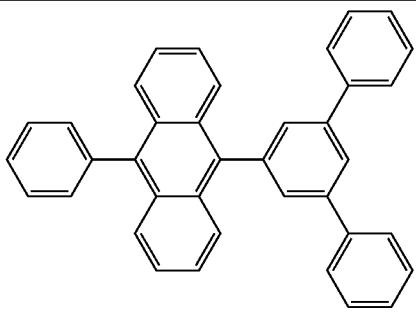

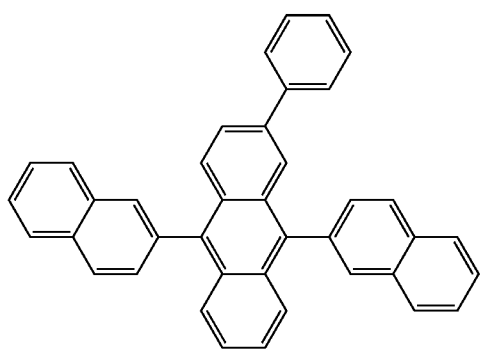 [SMILES: c1ccc(-c2ccc3c(-c4ccc5ccccc5c4)c4ccccc4c(-c4ccc5ccccc5c4)c3c2)cc1]

Suitable phosphorescent compounds are, in particular, compounds which emit light, preferably in the visible region, on suitable excitation and in addition contain at least one atom having an atomic number of greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum. For the purposes of the present application, all luminescent metal complexes which contain the above-mentioned metal are referred to as phosphorescent compounds.

Examples of suitable phosphorescent emitters are revealed by the applications WO 00/70655, WO 01/41512, WO 02/02714, WO 02/15645, EP 1191613, EP 1191612, EP 1191614, WO 04/081017, WO 05/033244, WO 05/042550, WO 05/113563, WO 06/008069, WO 06/061182, WO 06/081973 and the unpublished application DE 102008027005.9. In general, all phosphorescent complexes as used in accordance with the prior art for phosphorescent OLEDs and as are known to the person skilled in the art in the area of organic electroluminescence are suitable, and the person skilled in the art will be able to use further phosphorescent compounds without inventive step.

Suitable matrix materials for the phosphorescent emitters are selected from the group consisting of aromatic ketones, phosphine oxides, sulfoxides and sulfones, for example in accordance with WO 04/013080, WO 04/093207, WO 06/005627 or the unpublished application DE 102008033943.1, triarylamines, carbazole derivatives, for example CBP (N,N-biscarbazolylbiphenyl) or the carbazole derivatives disclosed in WO 05/039246, US 2005/0069729, JP 2004/288381, EP 1205527 or WO 08/086851, cis- and trans-indolocarbazole derivatives, for example in accordance with WO 07/063754 or WO 08/056746, azacarbazoles, for example in accordance with EP 1617710, EP 1617711, EP 1731584, JP 2005/347160, bipolar matrix materials, for example in accordance with WO 07/137725, silanes, for example in accordance with WO 05/111172, azaboroles or boronic esters, for example in accordance with WO 06/117052, triazine derivatives, for example in accordance with the unpublished application DE 102008036982.9, WO 07/063754 or WO 08/056746, and zinc complexes, for example in accordance with WO 09/062578.

Apart from the materials according to the invention, suitable charge-transport materials, as can be used in the hole-injection or hole-transport layer or in the electron-transport layer of the organic electroluminescent device according to the invention, are, for example, the compounds disclosed in Y. Shirota et al., *Chem. Rev.* 2007, 107(4), 953-1010, or other materials, as employed in accordance with the prior art in these layers.

Examples of preferred hole-transport materials which can be used in a hole-transport or hole-injection layer in the electroluminescent device according to the invention are indenofluorenamines and derivatives (for example in accordance with WO 06/122630, WO 06/100896 or the unpublished application DE 102008024182.2), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449) or dibenzoindenofluorenamines (for example in accordance with WO 07/140847). Hole-transport and hole-injection materials which are furthermore suitable are derivatives of the above-mentioned compounds, as disclosed in JP 2001/226331, EP 676461, EP 650955, WO 01/049806, U.S. Pat. No. 4,780,536, WO 98/30071, EP 891121, EP 1661888, JP 2006/253445, EP 650955, WO 06/073054 and U.S. Pat. No. 5,061,569.

Suitable hole-transport or hole-injection materials are furthermore, for example, the materials indicated in the following table.

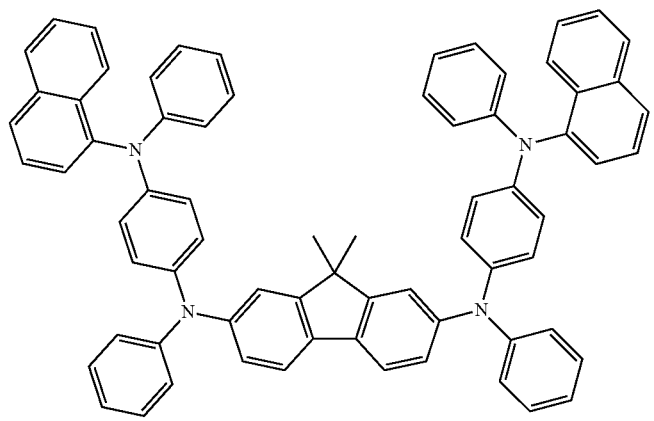 [SMILES: CC1(C)c2cc(N(c3ccccc3)c3ccc(N(c4ccccc4)c4cccc5ccccc45)cc3)ccc2-c2ccc(N(c3ccccc3)c3ccc(N(c4ccccc4)c4cccc5ccccc45)cc3)cc21]
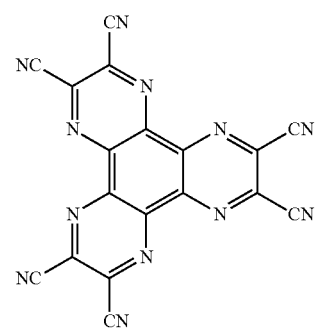 [SMILES: N#Cc1nc2c3nc(C#N)c(C#N)nc3c3nc(C#N)c(C#N)nc3c2nc1C#N]
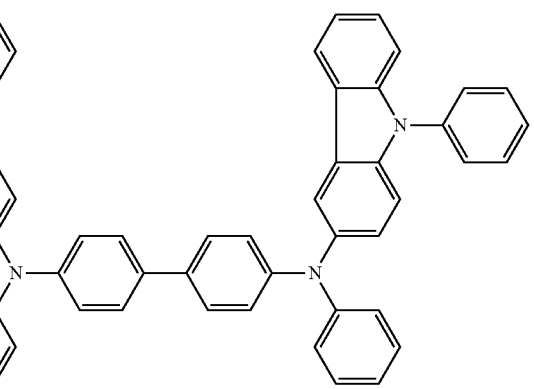

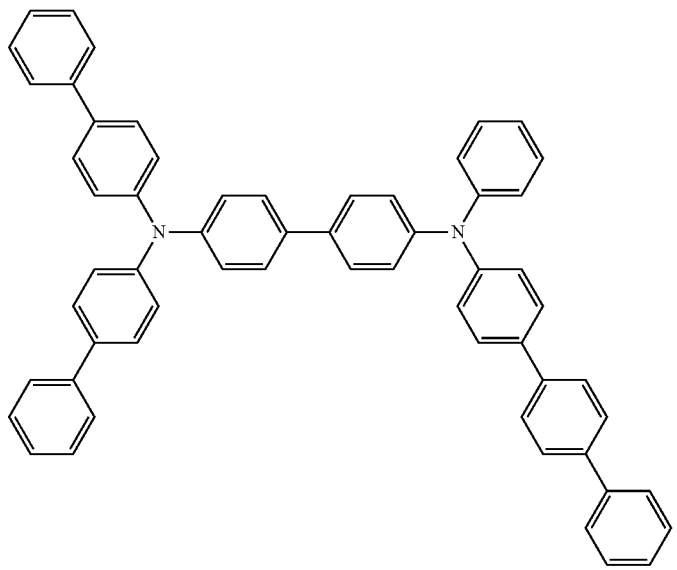 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1]
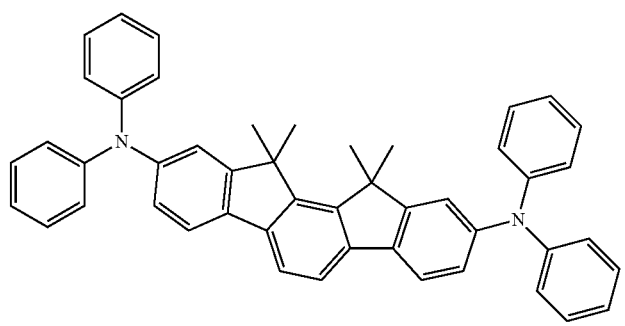 [SMILES: CC1(C)c2cc(N(c3ccccc3)c3ccccc3)ccc2-c2ccc3c(c21)C(C)(C)c1cc(N(c2ccccc2)c2ccccc2)ccc1-3]
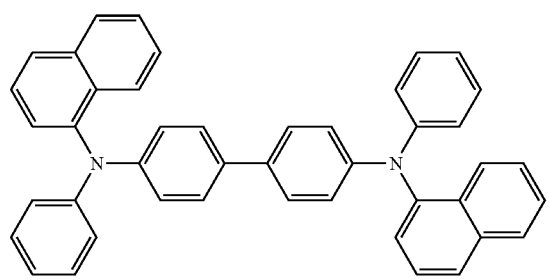 [SMILES: c1ccc(N(c2ccc(-c3ccc(N(c4ccccc4)c4cccc5ccccc45)cc3)cc2)c2cccc3ccccc23)cc1]
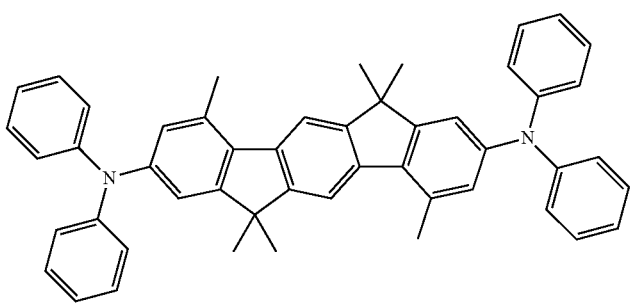 [SMILES: Cc1cc(N(c2ccccc2)c2ccccc2)cc2c1-c1cc3c(cc1C2(C)C)-c1c(C)cc(N(c2ccccc2)c2ccccc2)cc1C3(C)C]

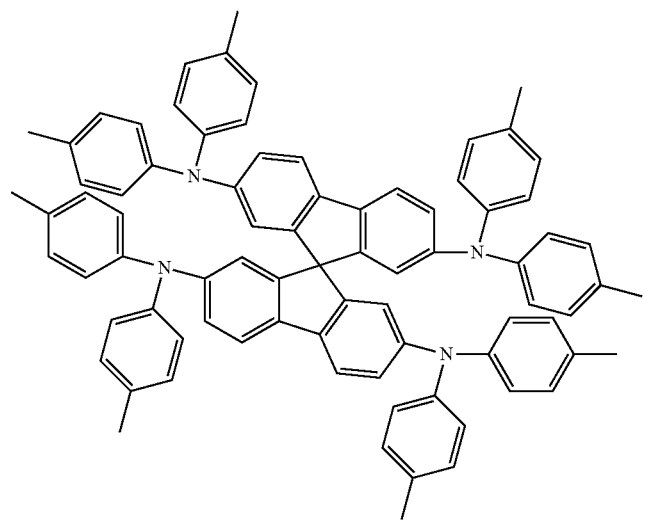
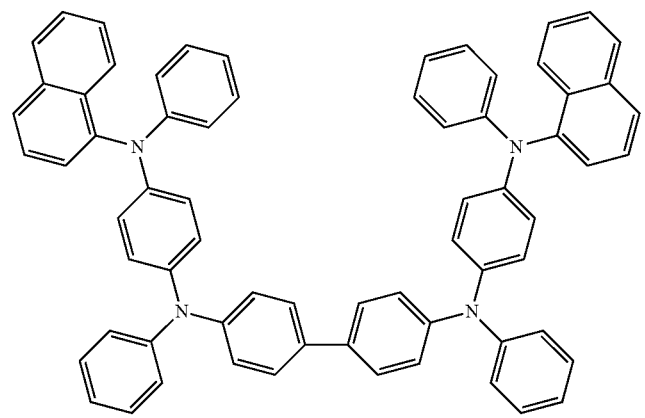 [SMILES: c1ccc(N(c2ccc(-c3ccc(N(c4ccccc4)c4ccc(N(c5ccccc5)c5cccc6ccccc56)cc4)cc3)cc2)c2ccc(N(c3ccccc3)c3cccc4ccccc34)cc2)cc1]
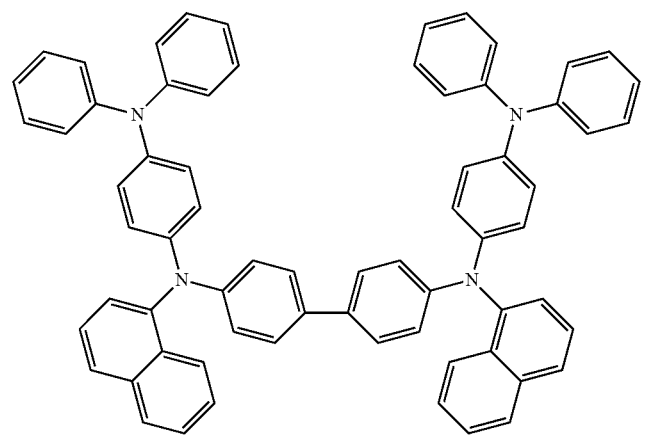 [SMILES: c1ccc(N(c2ccccc2)c2ccc(N(c3ccc(-c4ccc(N(c5ccc(N(c6ccccc6)c6ccccc6)cc5)c5cccc6ccccc56)cc4)cc3)c3cccc4ccccc34)cc2)cc1]

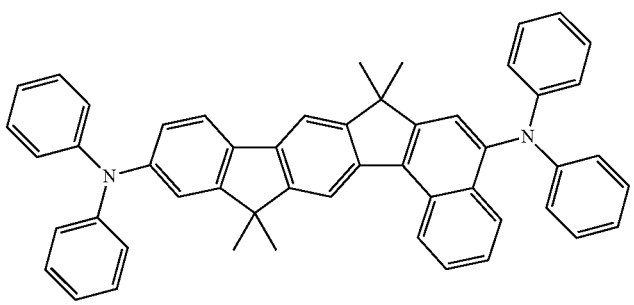 [SMILES: CC1(C)c2cc(N(c3ccccc3)c3ccccc3)ccc2-c2cc3c(cc21)-c1c(cc(N(c2ccccc2)c2ccccc2)c2ccccc12)C3(C)C]
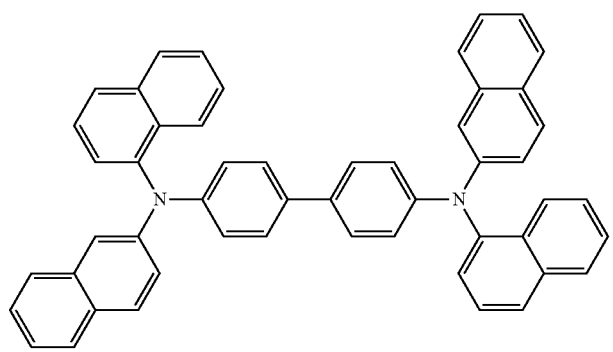 [SMILES: c1ccc2cc(N(c3ccc(-c4ccc(N(c5ccc6ccccc6c5)c5cccc6ccccc56)cc4)cc3)c3cccc4ccccc34)ccc2c1]
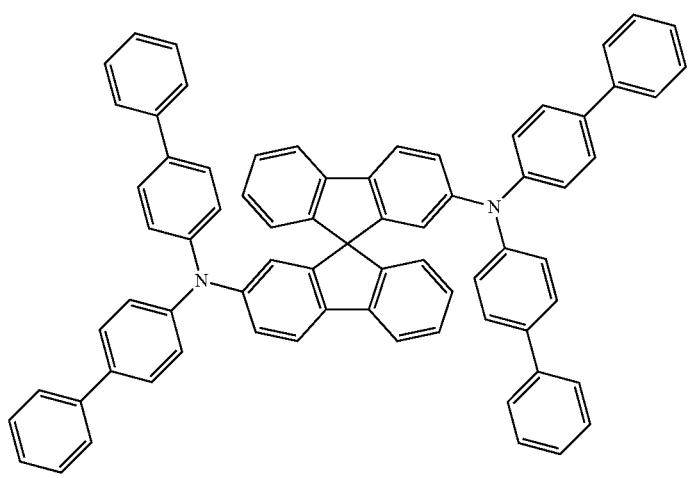 [SMILES: c1ccc(-c2ccc(N(c3ccc(-c4ccccc4)cc3)c3ccc4c(c3)C3(c5ccccc5-4)c4ccccc4-c4ccc(N(c5ccc(-c6ccccc6)cc5)c5ccc(-c6ccccc6)cc5)cc43)cc2)cc1]
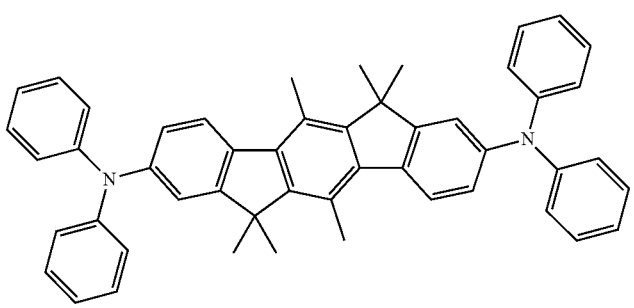 [SMILES: Cc1c2c(c(C)c3c1C(C)(C)c1cc(N(c4ccccc4)c4ccccc4)ccc1-3)C(C)(C)c1cc(N(c3ccccc3)c3ccccc3)ccc1-2]

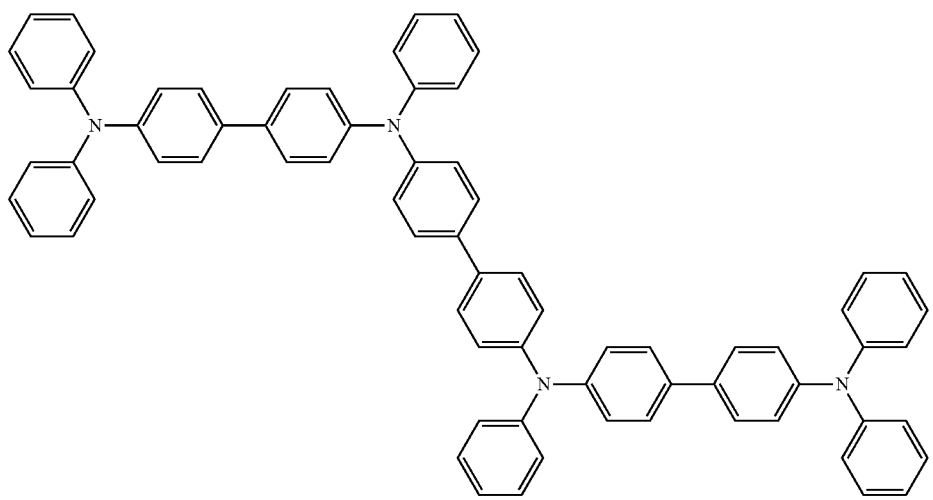 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1]
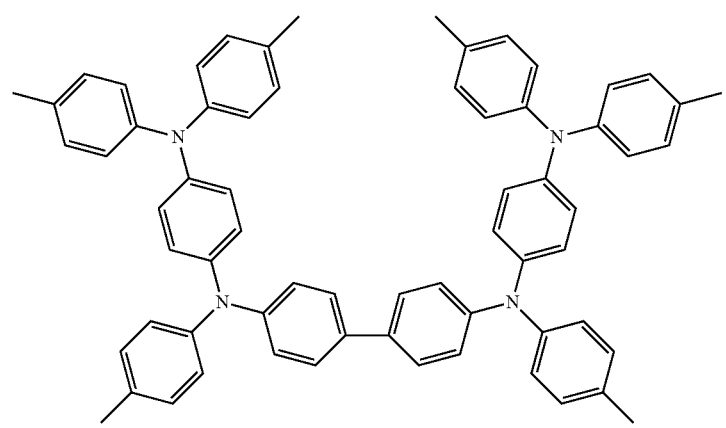
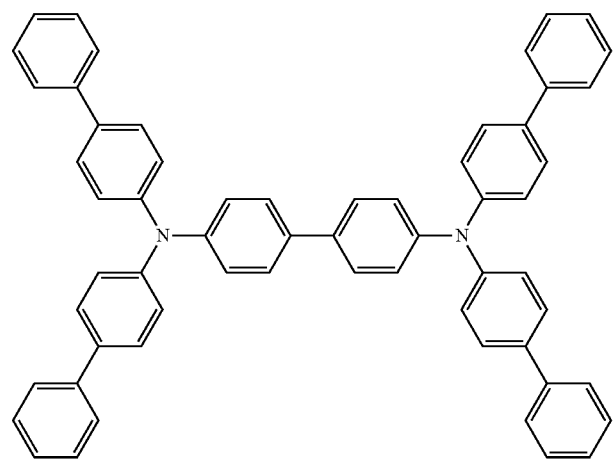 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]

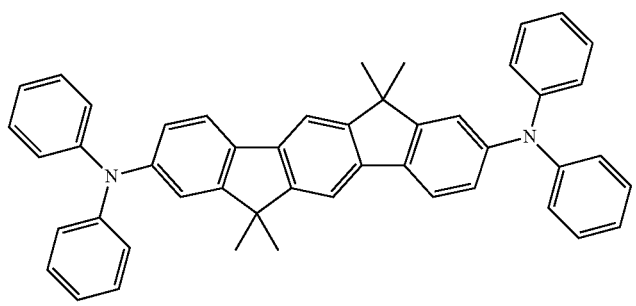 [SMILES: CC1(C)c2cc(N(c3ccccc3)c3ccccc3)ccc2-c2cc3c(cc21)-c1ccc(N(c2ccccc2)c2ccccc2)cc1C3(C)C]
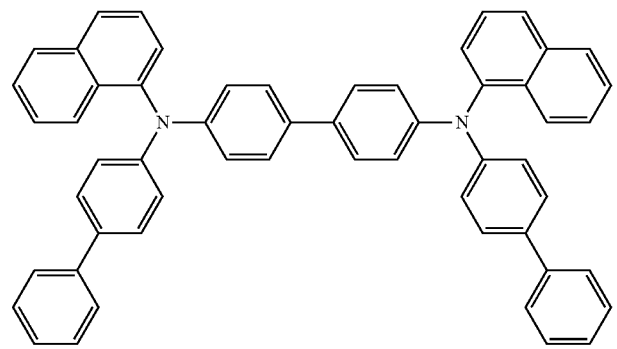 [SMILES: c1ccc(-c2ccc(N(c3ccc(-c4ccc(N(c5ccc(-c6ccccc6)cc5)c5cccc6ccccc56)cc4)cc3)c3cccc4ccccc34)cc2)cc1]
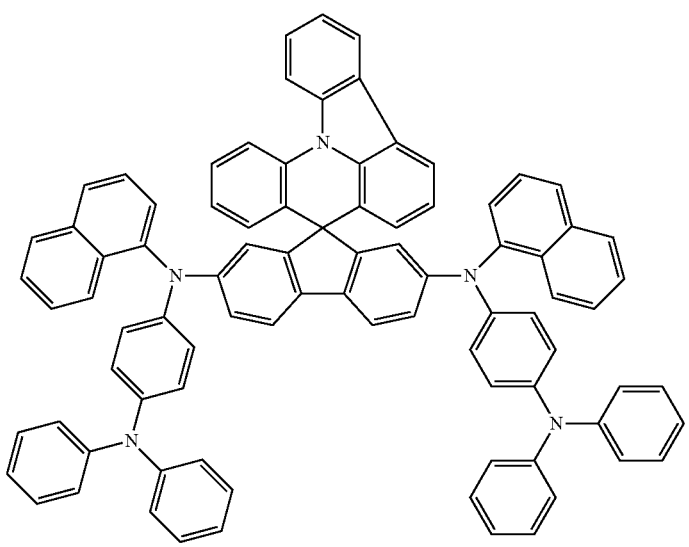 [SMILES: c1ccc(N(c2ccccc2)c2ccc(N(c3ccc4c(c3)C3(c5cc(N(c6ccc(N(c7ccccc7)c7ccccc7)cc6)c6cccc7ccccc67)ccc5-4)c4ccccc4-n4c5ccccc5c5cccc3c54)c3cccc4ccccc34)cc2)cc1]
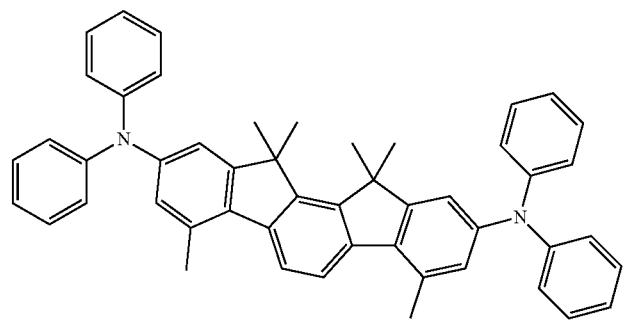 [SMILES: Cc1cc(N(c2ccccc2)c2ccccc2)cc2c1-c1ccc3c(c1C2(C)C)C(C)(C)c1cc(N(c2ccccc2)c2ccccc2)cc(C)c1-3]

Suitable electron-transport or electron-injection materials which can be used in the electroluminescent device according to the invention are, for example, the materials indicated in the following table. Electron-transport and electron-injection materials which are furthermore suitable are derivatives of the compounds depicted above, as disclosed in JP 2000/053957, WO 03/060956, WO 04/028217 and WO 04/080975.

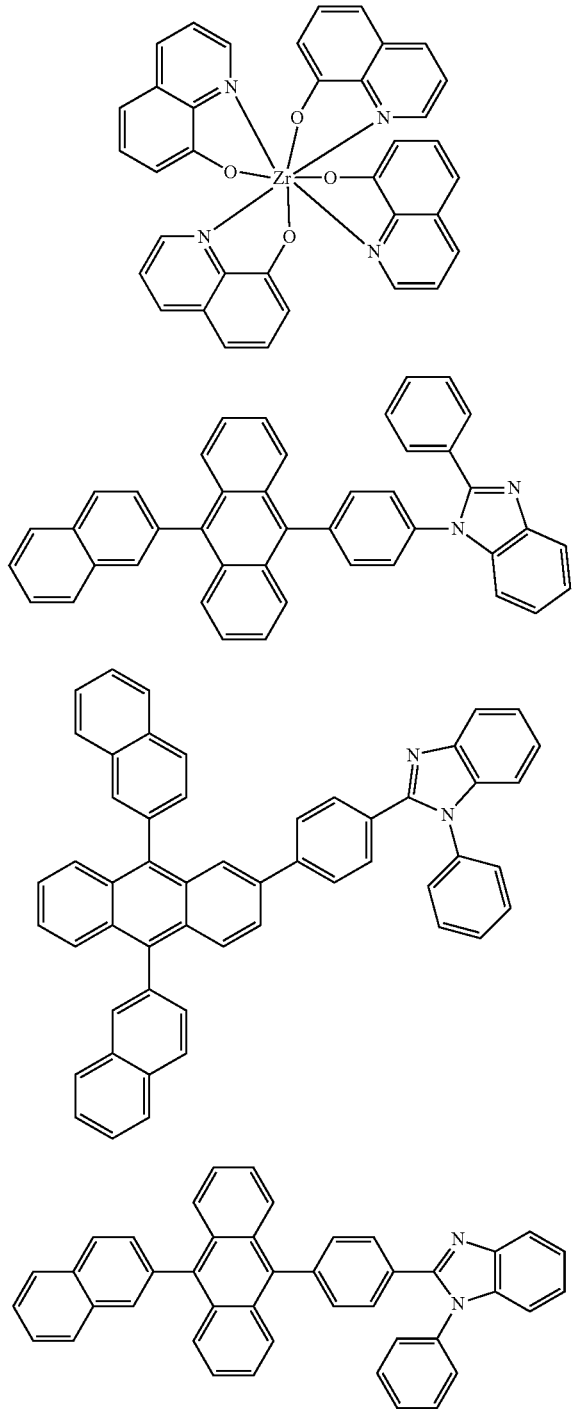

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it should be noted that the initial pressure may also be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds are necessary for this purpose. High solubility can be achieved through suitable substitution of the compounds. It is not only solutions of individual materials that can be applied here, but also solutions which comprise a plurality of compounds, for example matrix material and dopant.

It is also possible to combine a plurality of these processes and, for example, to apply one or more layers by vapour deposition and to apply one or more further layers from solution.

The present invention furthermore relates to the processes mentioned above.

The compounds according to the invention have the following surprising advantages over the prior art on use in organic electroluminescent devices:

1. The compounds of the formulae (1) to (6) have high thermal stability and can be sublimed without decomposition.
2. The compounds of the formulae (1) to (6), in particular compounds of the formula (3), which are substituted by electron-deficient substituents, in particular F, CN and/or electron-deficient heterocycles, are very highly suitable as hole-injection material or as hole-transport material for use in a hole-injection layer or in a hole-transport layer and result in high efficiencies, in particular in high power efficiencies, and long life-times in this use.
3. The compounds of the formulae (1) to (6), in particular those which are substituted by aromatic or heteroaromatic groups, are very highly suitable as electron-transport material or as hole-blocking material for use in an electron-transport layer or in a hole-blocking layer and result in high efficiencies, in particular in high power efficiencies, and long life-times in this use.
4. The compounds of the formulae (1) to (6), in particular those which are substituted by aromatic or heteroaromatic groups, are very highly suitable as matrix material for emitting compounds, in particular for phosphorescent compounds, for use in an emitting layer.
5. The compounds of the formulae (1) to (6) have very high photostability, i.e. do not decompose on exposure to light, and are therefore very highly suitable for use both in organic electroluminescent devices and in organic solar cells.

The invention is described in greater detail by the following examples, without wishing to restrict it thereby. The person skilled in the art will be able to produce further organic electronic devices according to the invention, in particular organic electroluminescent devices, without inventive step.

EXAMPLES

The following syntheses are—unless indicated otherwise—carried out under a protective-gas atmosphere in dried solvents. The solvents and reagents can be purchased from ALDRICH or ABCR. The precursor trichloroheptaazaphenalene can be prepared in accordance with EP 1854797. Triphenylheptaazaphenalene and trimesitylheptaazaphenalene can be prepared by the method of H. Schröder et al., *J. Org. Chem.* 1962, 27, 4262-4266.

Example 1

Synthesis of tricyanoheptaazaphenalene (HIM-1)

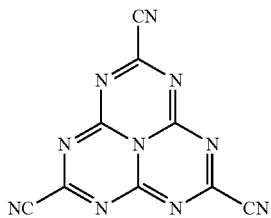

50 g (181 mmol) of trichloroheptaazaphenalene and 53.45 g (597 mmol, 3.3 equivalents) of copper(I) cyanide are suspended in 750 ml of DMF and heated at 130° C. for 60 h under argon. After cooling to room temperature, the reaction mixture is added to 1000 ml of concentrated ammonia solution and stirred vigorously in air for 4 h. The organic precipitate which deposits in the process is filtered off with suction and washed with cold ethanol. The residue is extracted with acetonitrile in a Soxhlet apparatus, the precipitate which crystallises out is filtered off with suction, washed with a little cold acetonitrile and dried in vacuo. Yield: 39.1 g (157 mmol), 87% of theory; purity about 99.8% (HPLC).

Example 2

Production and Characterisation of Organic Electroluminescent Devices

OLEDs according to the invention are produced by a general process in accordance with WO 04/058911, which is adapted to the circumstances described here (layer-thickness variation, materials used).

In Examples 3 to 8 below, the results for various OLEDs are presented. Glass plates coated with structured ITO (indium-tin oxide) form the substrates of the OLEDs. For improved processing, 20 nm of PEDOT (spin-coated from water; purchased from H. C. Starck, Goslar, Germany; poly-(3,4-ethylenedioxy-2,5-thiophene)) are applied to the substrate. The OLEDs consist of the following layer sequence: substrate/PEDOT 20 nm/hole-injection layer (HIL) 5 nm/hole-transport layer (HTL-1) 20 nm/hole-transport layer (HTL-2) 20 nm/emission layer (EML) 30 nm/electron-transport layer (ETL) 20 nm and finally a cathode.

The materials apart from PEDOT are applied by thermal vapour deposition in a vacuum chamber. The emission layer here always consists of a matrix material (host) and a dopant, which is admixed with the host by co-evaporation. The matrix material used in Examples 3 to 8 described below is compound H1, which is in each case doped with 10% of D1. These OLEDs exhibit green emission. The hole-transport material used in HTL-1 is compound HTM-1. The hole-transport material used in HTL-2 is NPB. The cathode is formed by an LiF layer with a thickness of 1 nm and an Al layer with a thickness of 100 nm deposited on top. Table 1 shows the chemical structures of the materials used to build up the OLEDs.

These OLEDs are characterised by standard methods; for this purpose, the electroluminescence spectra, the efficiency (measured in cd/A), the power efficiency (measured in lm/W) as a function of the luminance, calculated from current-voltage-luminance characteristic lines (IUL characteristic lines), and the lifetime are determined. The lifetime is defined as the time after which the initial luminance of 25,000 cd/m² has dropped to half. The use voltage is defined as the voltage at which the OLED achieves a luminance of 1 cd/m².

Table 2 shows the results for some OLEDs (Examples 3 to 8). The hole-injection material used in accordance with the invention in the hole-injection layer (HIL) is HIM-1 (tricyanoheptaazaphenalene, from Example 1) or HIM-2 (hexacyanohexaazatriphenylene, in accordance with the prior art). Compared with the prior art, OLEDs which comprise HIM-1 in the hole-injection layer are distinguished by improved efficiency, in particular improved power efficiency, and lifetime compared with HIM-2 in accordance with the prior art. The use voltage and colour coordinates on use according to the invention of HIM-1 are very similar to those on use of HIM-2 in accordance with the prior art.

The electron-transport material employed in the electron-transport layer (ETL) is either AlQ$_3$ in accordance with the prior art or, in accordance with the invention, triphenylheptaazaphenalene (ETM-1) or trimesitylheptaazaphenalene (ETM-2).

TABLE 1

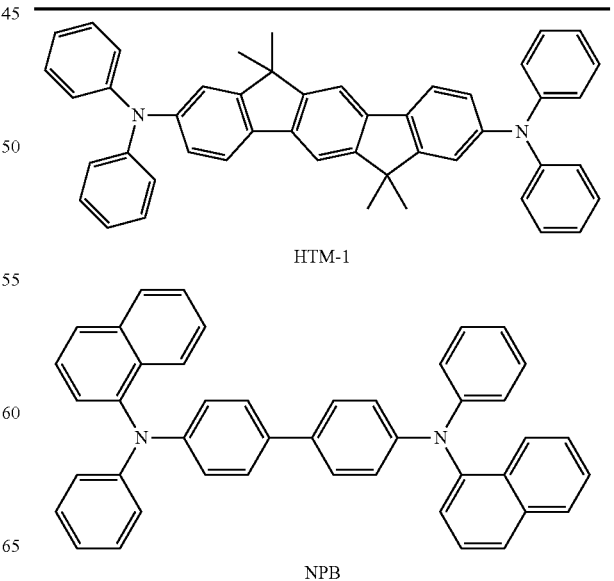

TABLE 1-continued
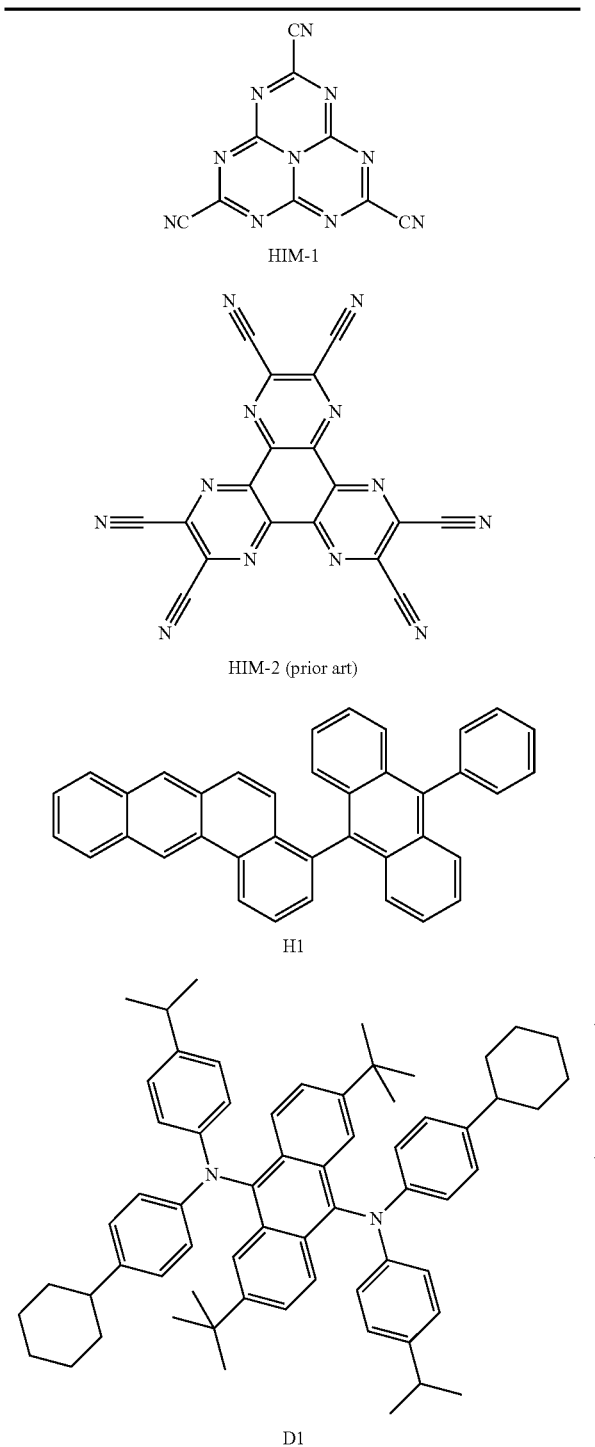
TABLE 1-continued
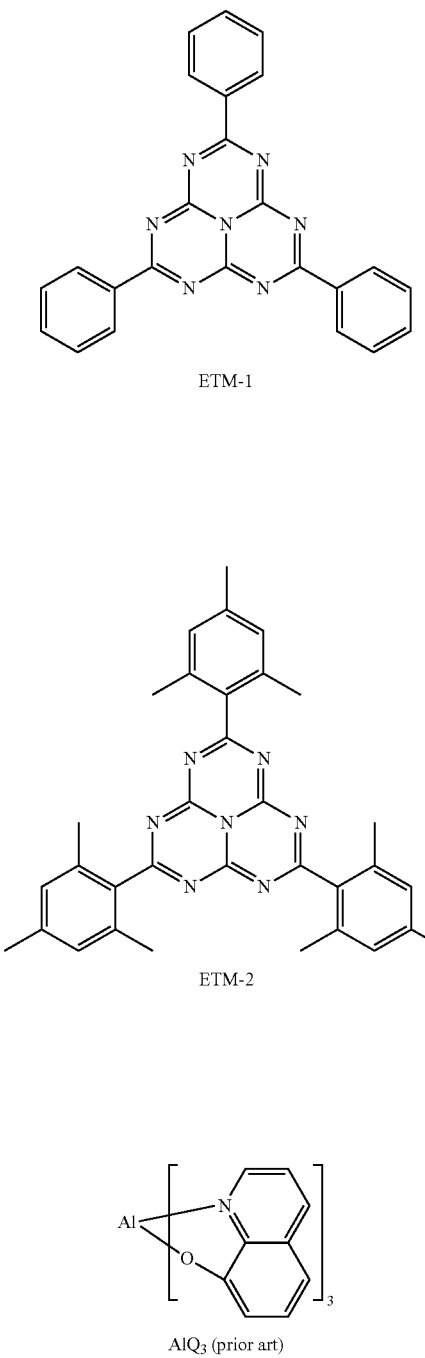
TABLE 2
| Ex. | HIL | ETL | Use voltage | Voltage for 1000 cd/m$^2$ | Efficiency at 1000 cd/m$^2$ | Power efficiency at 1000 cd/m$^2$ | CIE x/y at 1000 cd/m$^2$ | Lifetime for 25000 cd/m$^2$ |
|---|---|---|---|---|---|---|---|---|
| 3 | HIM-1 | AlQ$_3$ | 2.7 V | 4.8 V | 18.9 cd/A | 12.4 lm/W | 0.34/0.63 | 410 h |
| 4 (comp.) | HIM-2 | AlQ$_3$ | 2.8 V | 5.0 V | 17.1 cd/A | 10.7 lm/W | 0.34/0.62 | 355 h |

TABLE 2-continued

| Ex. | HIL | ETL | Use voltage | Voltage for 1000 cd/m² | Efficiency at 1000 cd/m² | Power efficiency at 1000 cd/m² | CIE x/y at 1000 cd/m² | Lifetime for 25000 cd/m² |
|---|---|---|---|---|---|---|---|---|
| 5 | HIM-1 | ETM-1 | 2.8 V | 5.0 V | 19.2 cd/A | 12.1 lm/W | 0.33/0.62 | 445 h |
| 6 | HIM-1 | ETM-2 | 2.6 V | 4.6 V | 21.3 cd/A | 14.5 lm/W | 0.33/0.62 | 440 h |
| 7 | HIM-2 | ETM-1 | 2.8 V | 5.1 V | 18.2 cd/A | 11.2 lm/W | 0.34/0.62 | 390 h |
| 8 | HIM-2 | ETM-2 | 2.7 V | 4.8 V | 20.2 cd/A | 13.2 lm/W | 0.34/0.63 | 375 h |

The invention claimed is:

1. An organic electronic device comprising a cathode, an anode and at least one organic layer, which is arranged between the cathode and anode and which comprises at least one compound of the formula (1) or formula (2):

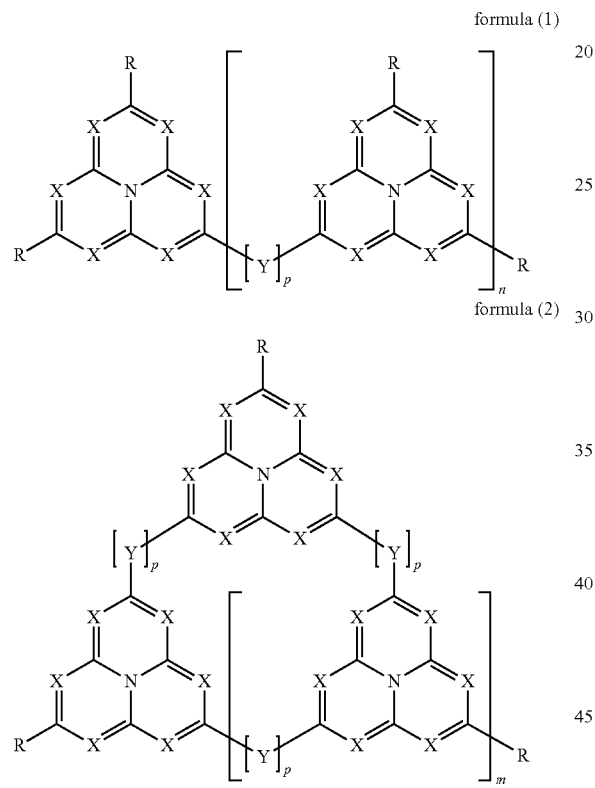

where the following applies to the symbols and indices used:

X is on each occurrence, identically or differently, $CR^1$ or N;

Y is on each occurrence, identically or differently, a divalent group selected from the group consisting of $B(R^1)_2$, $C(R^1)_2$, $NR^1$, O, S, C(=O), C=C($R^1$)$_2$, S(=O), S(=O)$_2$, P(=O)($R^1$)$_2$, and a divalent aromatic or heteroaromatic ring system having 5 to 18 aromatic ring atoms, which is optionally substituted by one or more radicals $R^1$;

R is on each occurrence, identically or differently, H, D, F, Cl, Br, I, CHO, $N(R^1)_2$, $N(Ar)_2$, C(=O)Ar, P(=O)(Ar)$_2$, S(=O)Ar, S(=O)$_2$Ar, $CR^1$=$CR^1$Ar, CN, NO$_2$, Si($R^1$)$_3$, B(OR$^1$)$_2$, B($R^1$)$_2$, B(Ar)$_2$, B(N($R^1$)$_2$)$_2$, OSO$_2$R$^1$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which is optionally substituted by one or more radicals $R^1$, where one or more non-adjacent CH$_2$ groups is optionally replaced by $R^1$C=$CR^1$, C≡C, Si($R^1$)$_2$, Ge($R^1$)$_2$, Sn($R^1$)$_2$, C=O, C=S, C=Se, C=$NR^1$, P(=O)($R^1$), SO, SO$_2$, NR$^1$, O, S or CONR$^1$ and where one or more H atoms is optionally replaced by D, F, Cl, Br, I, CN or NO$_2$, or an aromatic or heteroaromatic ring system having 5 to 60 aromatic ring atoms, which may in each case be substituted by one or more radicals $R^1$, or an aryloxy or heteroaryloxy group having 5 to 60 aromatic ring atoms, which may in each case be substituted by one or more radicals $R^1$, or a combination of these systems;

$R^1$ is on each occurrence, identically or differently, H, D, F, Cl, Br, I, CHO, $N(R^2)_2$, $N(Ar)_2$, C(=O)Ar, P(=O)(Ar)$_2$, S(=O)Ar, S(=O)$_2$Ar, $CR^2$=$CR^2$Ar, CN, NO$_2$, Si($R^2$)$_3$, B(OR$^2$)$_2$, B($R^2$)$_2$, B(N($R^2$)$_2$)$_2$, OSO$_2$R$^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which is optionally substituted by one or more radicals $R^2$, where one or more non-adjacent CH$_2$ groups is optionally replaced by $R^2$C=$CR^2$, C≡C, Si($R^2$)$_2$, Ge($R^2$)$_2$, Sn($R^2$)$_2$, C=O, C=S, C=Se, C=$NR^2$, P(=O)($R^2$), SO, SO$_2$, NR$^2$, O, S or CONR$^2$ and where one or more H atoms is optionally replaced by D, F, Cl, Br, I, CN or NO$_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a combination of these systems;

Ar is on each occurrence, identically or differently, an aromatic or heteroaromatic ring system having 5 to 30 aromatic ring atoms, which is optionally substituted by one or more non-aromatic radicals $R^1$; two radicals Ar which are bonded to the same nitrogen or phosphorus atom which is optionally linked to one another here by a single bond or a bridge selected from B($R^2$), C($R^2$)$_2$, Si($R^2$)$_2$, C=O, C=$NR^2$, C=C($R^2$)$_2$, O, S, S=O, SO$_2$, N($R^2$), P($R^2$) and P(=O)$R^2$;

$R^2$ is on each occurrence, identically or differently, H, D or an aliphatic, aromatic and/or heteroaromatic hydrocarbon radical having 1 to 20 C atoms, in which, in addition, H atoms is optionally replaced by F; two or more adjacent substituents $R^2$ here optionally form a mono- or polycyclic, aliphatic or aromatic ring system with one another;

n is 0, 1, 2, 3, 4, 5 or 6;

m is 0, 1, 2 or 3;

p is on each occurrence, identically or differently, 0, 1, 2 or 3 and wherein the compounds of the formula (1) or formula (2) are employed as electron-transport material or as hole-blocking material in an electron-transport layer or hole-blocking layer or as charge-generation material in a charge-generation layer and wherein the organic electronic device is selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O—SCs), organic optical detectors, organic photoreceptors, organic field-quench devices (O-FQDs), light-emitting electrochemical cells (LECs) and organic laser diodes (O-lasers).

2. The organic electronic device according to claim 1, wherein the compound of the formula (1) or of the formula (2) is selected from the compounds of the formula (3), formula (4), formula (5) or formula (6):

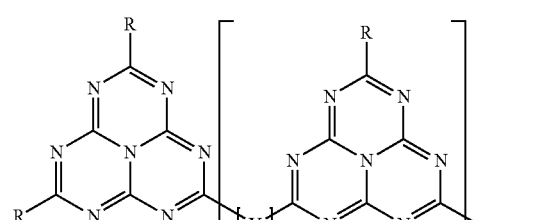

formula (3)

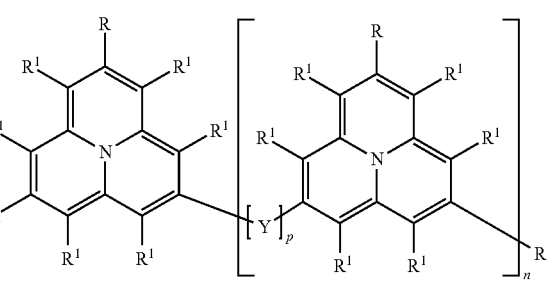

formula (4)

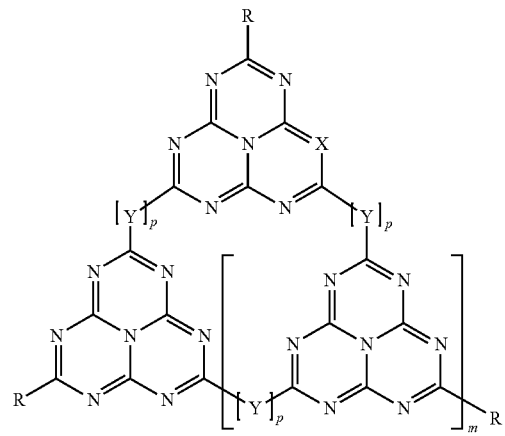

formula (5)

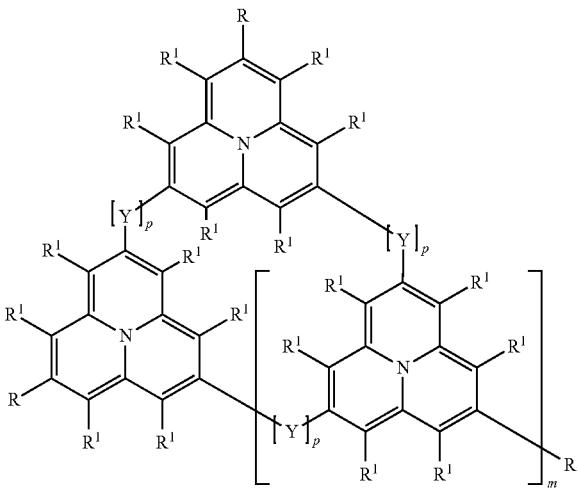

formula (6)

where the symbols and indices used have the same meaning as described in claim 1.

3. The organic electronic device according to claim 2, wherein $R^1$ in formula (4) and formula (6) stands for hydrogen or deuterium.

4. The organic electronic device according to claim 2, wherein the index n in compounds of the formulae (1), (3) and (4) stands for 0, 1 or 2 and in that the index m in the compounds of the formulae (2), (5) and (6) stands for 0, 1 or 2.

5. The organic electronic device according to claim 2, wherein the index n in compounds of the formulae (1), (3) and (4) stands for 0, and in that the index m in the compounds of the formulae (2), (5) and (6) stands for 1.

6. The organic electronic device according to claim 2, wherein Y in compounds of the formulae (1) to (6), if p is not equal to 0, stands, identically or differently on each occurrence, for a divalent group selected from the group consisting of $C(R^1)_2$, $NR^1$ and a divalent aryl or heteroaryl group having 5 to 14 aromatic ring atoms, which may be substituted by one or more radicals $R^1$.

7. The organic electronic device according to claim 2, wherein R in the compounds of the formulae (1) to (6) stands, identically or differently on each occurrence, for F, $N(R^1)_2$, $N(Ar)_2$, $C(=O)Ar$, $P(=O)(Ar)_2$, CN, $NO_2$, a straight-chain alkyl group having 1 to 10 C atoms or a branched or cyclic alkyl group having 3 to 10 C atoms, each of which is optionally substituted by one or more radicals $R^1$, where one or more H atoms is optionally replaced by F or CN, or an aromatic or heteroaromatic ring system having 5 to 40 aromatic ring atoms, which may in each case be substituted by one or more radicals $R^1$.

8. The organic electronic device according to claim 7, wherein R in the compounds of the formulae (1) to (6) stands, identically or differently on each occurrence, for F, CN, $CF_3$ or an aromatic or heteroaromatic ring system having 5 to 30 aromatic ring atoms, which may in each case be substituted by one or more radicals $R^1$.

9. The organic electronic device according to claim 7, wherein R in the compounds of the formulae (1) to (6) stands, identically or differently on each occurrence, for F, CN, $CF_3$ or phenyl, 2-, 3- or 4-pyridyl, pyrazinyl, 2-, 4- or 5-pyrimidinyl, 3- or 4-pyridazinyl, ortho-, meta- or para-biphenyl, ortho-, meta- or para-terphenyl, 2-fluorenyl, 2-spirobifluorenyl, 1-naphthyl, 2-naphthyl, anthracenyl, phenylanthracenyl, 1- or 2-naphthyl-anthracenyl, binaphthyl, pyrenyl, fluoranthenyl, 2-, 3-, 4-, 5-, 6- or 7-benzanthracenyl, N-imidazolyl, N-benzimidazolyl, phenyl-N-benzimidazolyl, N-phenylbenzimidazolyl, phenyl-N-phenylbenzimidazolyl, or combinations of these groups, each of which is optionally substituted by one or more radicals $R^1$.

10. The organic electronic device according to claim 2, comprising an anode, a cathode and one or more emitting layers, where at least one organic layer comprises at least one compound of the formulae (1) to (6) or a corresponding oligomer, polymer or dendrimer, and one or more further layers selected from the group consisting of hole-injection layers, hole-transport layers, hole-blocking layers, electron-transport layers, electron-injection layers, electron-blocking layers, exciton-blocking layers, charge-generation layers and organic or inorganic p/n junctions, where these layers may also be doped.

11. The organic electronic device according to claim 10, wherein the compounds of the formulae (1) to (6) are used as hole-injection or hole-transport material.

12. The organic electronic device according to claim 10, wherein the compounds of the formulae (1) to (6) are used as hole-injection or hole-transport material, where all three substituents R, stand for an electron-deficient group.

13. The organic electronic device according to claim 12, wherein the substituents R are selected from the group consisting of CN, F, $NO_2$, $CF_3$ and substituted or unsubstituted electron-deficient heterocycles, where the electron-deficient heterocycles are selected from the group consisting of pyridine, pyrazine, pyrimidine, pyridazine, triazine, pyrrole, imidazole, triazole, benzimidazole, quinoline, isoquinoline, quinoxaline, thiadiazole, thiazole and oxadiazole, each of which is optionally substituted by one or more groups $R^1$.

14. The organic electronic device according to claim 10, wherein the compounds of the formulae (1) to (6) are employed as electron-transport material or as hole-blocking material in an electron-transport layer or hole-blocking layer.

15. The organic electronic device according to claim 10, wherein the compounds of the formulae (1) to (6) are employed as electron-transport material or as hole-blocking material in an electron-transport layer or hole-blocking layer, if the substituents R stand, identically or differently on each occurrence, for an aromatic or heteroaromatic ring system, where the electron-transport layer or hole-blocking layer may also be doped.

16. The organic electronic device according to claim 10, wherein the compounds of the formulae (1) to (6) are employed as charge-generation material in a charge-generation layer.

17. The organic electronic device according to claim 1, wherein all radicals R are selected identically.

18. A process for the production of the organic electronic device according to claim 1, which comprises applying one or more layers by means of a sublimation process and/or in that one or more layers are applied by means of the OVPD (organic vapour phase deposition) process or with the aid of carrier-gas sublimation and/or in that one or more layers are produced from solution and/or by means of a printing process.

19. An organic electronic device comprising at least one oligomer, polymer or dendrimer which comprises one or more compounds of the formulae (1) to (6)

formula (1)

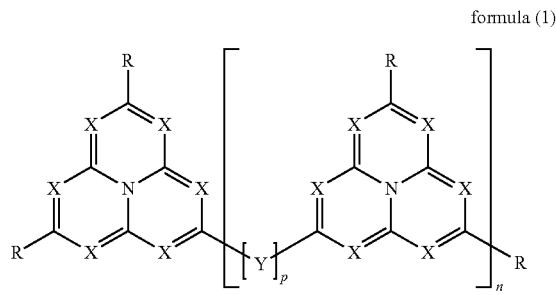

formula (2)

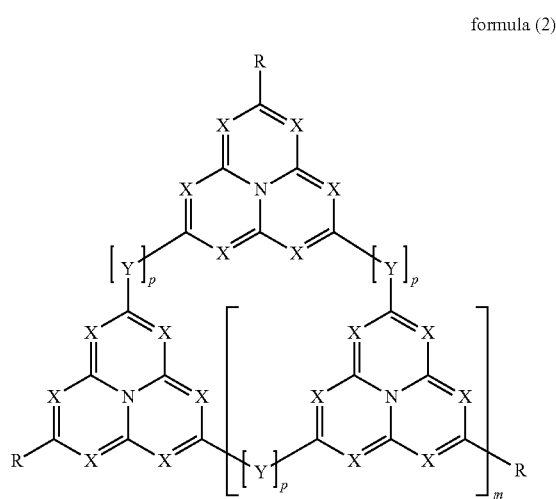

formula (3)

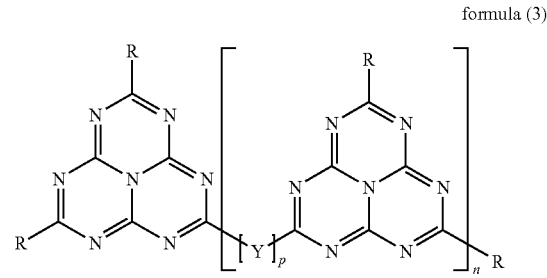

formula (4)

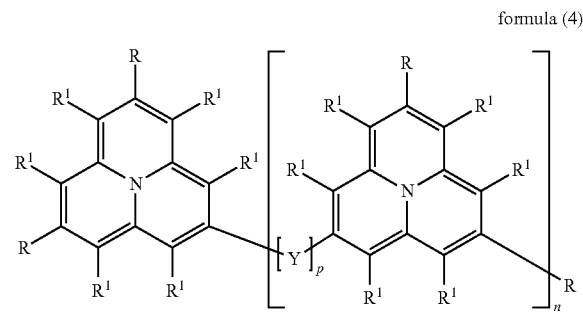

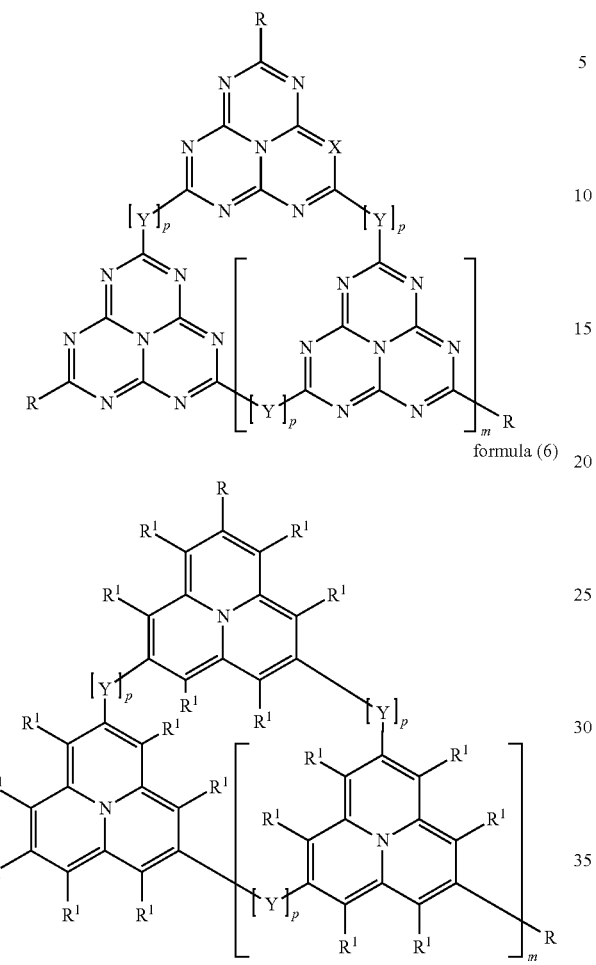

formula (5)

formula (6)

where the following applies to the symbols and indices used:

X is on each occurrence, identically or differently, $CR^1$ or N;

Y is on each occurrence, identically or differently, a divalent group selected from the group consisting of $B(R^1)_2$, $C(R^1)_2$, $NR^1$, O, S, C(=O), C=C($R^1)_2$, S(=O), S(=O)$_2$, P(=O)($R^1)_2$, and a divalent aromatic or heteroaromatic ring system having 5 to 18 aromatic ring atoms, which is optionally substituted by one or more radicals $R^1$;

R is on each occurrence, identically or differently, H, D, F, Cl, Br, I, CHO, N($R^1)_2$, N(Ar)$_2$, C(=O)Ar, P(=O)(Ar)$_2$, S(~0)Ar, S(=O)$_2$Ar, $CR^1$=$CR^1$Ar, CN, NO$_2$, Si($R^1)_3$, B(OR$^1)_2$, B($R^1)_2$, B(Ar)$_2$, B(N($R^1)_2)_2$, OSO$_2R^1$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which is optionally substituted by one or more radicals $R^1$, where one or more non-adjacent $CH_2$ groups is optionally replaced by $R^1C$=$CR^1$, Si($R^1)_2$, Ge($R^1)_2$, Sn($R^1)_2$, C=O, C=S, C=Se, C=$NR^1$, P(=O)($R^1$), SO, SO$_2$, $NR^1$, O, S or CONR$^1$ and where one or more H atoms is optionally replaced by D, F, Cl, Br, I, CN or NO$_2$, or an aromatic or heteroaromatic ring system having 5 to 60 aromatic ring atoms, which may in each case be substituted by one or more radicals $R^1$, or an aryloxy or heteroaryloxy group having 5 to 60 aromatic ring atoms, which may in each case be substituted by one or more radicals $R^1$, or a combination of these systems;

$R^1$ is on each occurrence, identically or differently, H, D, F, Cl, Br, I, CHO, N($R^2)_2$, N(Ar)$_2$, C(=O)Ar, P(=O)(Ar)$_2$, S(=O)Ar, S(=O)$_2$Ar, $CR^2$=$CR^2$Ar, CN, NO$_2$, Si($R^2)_3$, B(OR$^2)_2$, B($R^2)_2$, B(N($R^2)_2)_2$, OSO$_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which is optionally substituted by one or more radicals $R^2$, where one or more non-adjacent $CH_2$ groups is optionally replaced by $R^2C$=$CR^2$, Si($R^2)_2$, Ge($R^2)_2$, Sn($R^2)_2$, C=O, C=S, C=Se, C=$NR^2$, P(=O)($R^2$), SO, SO$_2$, $NR^2$, O, S or CONR$^2$ and where one or more H atoms is optionally replaced by D, F, Cl, Br, I, CN or NO$_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a combination of these systems;

Ar is on each occurrence, identically or differently, an aromatic or heteroaromatic ring system having 5 to 30 aromatic ring atoms, which is optionally substituted by one or more non-aromatic radicals $R^1$; two radicals Ar which are bonded to the same nitrogen or phosphorus atom which is optionally linked to one another here by a single bond or a bridge selected from B($R^2$), C($R^2)_2$, Si($R^2)_2$, C=O, C=$NR^2$, C=C($R^2)_2$, O, S, S=O, SO$_2$, N($R^2$), P($R^2$) and P(=O)$R^2$;

$R^2$ is on each occurrence, identically or differently, H, D or an aliphatic, aromatic and/or heteroaromatic hydrocarbon radical having 1 to 20 C atoms, in which, in addition, H atoms is optionally replaced by F; two or more adjacent substituents $R^2$ here optionally form a mono- or polycyclic, aliphatic or aromatic ring system with one another;

n is 0, 1, 2, 3, 4, 5 or 6;

m is 0, 1, 2 or 3;

p is on each occurrence, identically or differently, 0, 1, 2 or 3, where one or more radicals R represent bonds from the compound of the formulae (1) to (6) to the polymer, oligomer or dendrimer wherein the compounds of the formulae (1) to (6) are employed as electron-transport material or as hole-blocking material in an electron-transport layer or hole-blocking layer or as charge-generation material in a charge-generation layer, and wherein the organic electronic device is selected from the group consisting of organic electroluminescent devices (OLEDs), organic integrated circuits (G-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) and organic laser diodes (O-lasers).

* * * * *